United States Patent

Fujino et al.

[11] 4,277,394
[45] Jul. 7, 1981

[54] TETRAPEPTIDEHYDRAZIDE DERIVATIVES

[75] Inventors: Masahiko Fujino, Hyogo; Susumu Shinagawa, Osaka; Kiyohisa Kawai, Kyoto, all of Japan

[73] Assignee: Takeda Chemical Industries, Ltd, Osaka, Japan

[21] Appl. No.: 90,021

[22] Filed: Oct. 31, 1979

Related U.S. Application Data

[63] Continuation-in-part of Ser. No. 32,503, Apr. 23, 1979, abandoned.

[51] Int. Cl.$^3$ .................. C07C 103/52; C07G 7/00; A61K 37/00
[52] U.S. Cl. ........................... 260/112.5 R; 424/177
[58] Field of Search .............. 260/112.5 R, 112.5 E; 424/177

[56] References Cited

FOREIGN PATENT DOCUMENTS 7722097  2/1978  France ........................... 260/112.5 R

OTHER PUBLICATIONS

Dutta, A. S., et al., Life Sciences, vol. 21, pp. 559-562, 1977.
Coy, D., et al., Biochem. Biophys. Res. Comm., vol. 73, pp. 632-637, 1976.
Pert, A., Opiates and Endogenous Opioid Peptides, pp. 87-94, 1976.
Walker, J., et al., Science, vol. 196, pp. 85-87, 1977.
Roemer, D., et al., Nature, vol. 268, 547-549, 1977.
Belluzzi, J., et al., Life Sciences, vol. 23, pp. 99-104, 1978.
Bazusz, S., et al., FEBS Letters, vol. 76, pp. 91-92, 1977.
McGregor, W. H., et al., Life Sciences, vol. 23, pp. 1371-1378, 1978.

*Primary Examiner*—Delbert R. Phillips
*Assistant Examiner*—Blondel Hazel
*Attorney, Agent, or Firm*—Wegner & Bretschneider

[57] ABSTRACT

Novel tetrapeptidehydrazide derivatives, inclusive of a pharmacologically acceptable acid addition salt thereof, which has the general formula (I):

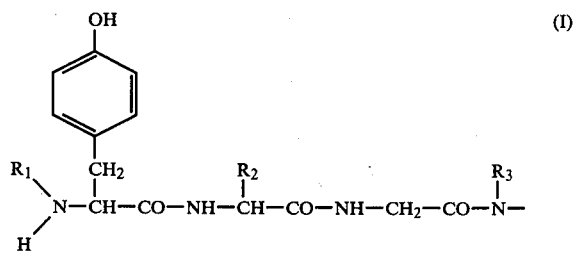

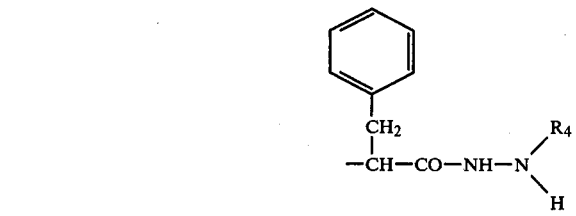

[wherein $R_1$ is hydrogen or lower alkyl; $R_2$ is hydrogen or the side chain of a D-α-amino acid; $R_3$ is hydrogen or lower alkyl; $R_4$ is hydrogen, or a saturated or unsaturated and straight or branched lower aliphatic acyl group which may optionally be substituted by hydroxy, amino, lower alkoxy, halogen, oxo, lower alkylthio or lower alkylthiooxide], are useful as analgesics.

90 Claims, No Drawings

TETRAPEPTIDEHYDRAZIDE DERIVATIVES

This is a continuation-in-part of application Ser. No. 32,503 filed Apr. 23, 1979, now abandoned.

The present invention is directed to:
(1) a tetrapeptide hydrazide derivative, inclusive of a pharmacologically acceptable acid addition salt thereof, which has the general formula (I):

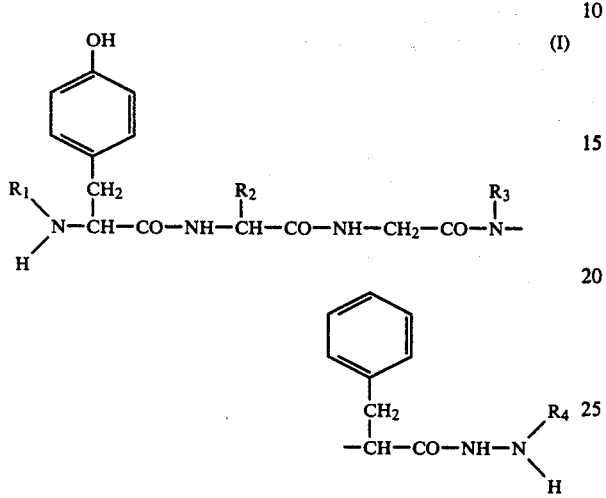

[wherein $R_1$ is hydrogen or lower alkyl; $R_2$ is hydrogen or the side chain of a D-α-amino acid; $R_3$ is hydrogen or lower alkyl; $R_4$ is hydrogen, or a saturated or unsaturated and straight or branched lower aliphatic acyl group which may optionally be substituted by hydroxy, amino, lower alkoxy, halogen, oxo, lower alkylthio or lower alkylthiooxide], (2) a method of producing a tetrapeptide hydrazide derivative of general formula (I) characterized by deprotecting a compound of general formula (II):

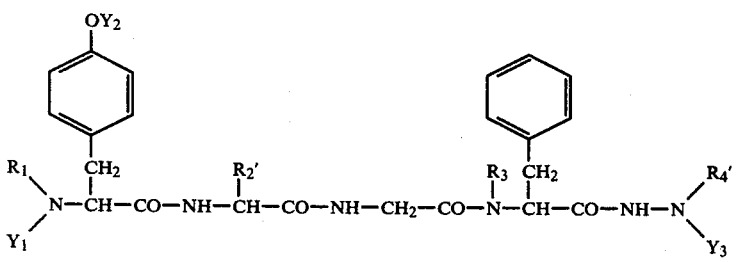

[wherein $R_1$ is hydrogen or lower alkyl; $R_2'$ is hydrogen or the side chain of a D-α-amino acid which may optionally be protected; $R_3$ is hydrogen or lower alkyl; $R_4'$ is hydrogen, or a saturated or unsaturated and straight or branched lower aliphatic acyl group which may optionally be substituted by hydroxy, amino, lower alkoxy, halogen, oxo, lower alkylthio or lower alkylthiooxide and which may be protected; $Y_1$ is a protective group; $Y_2$ and $Y_3$, respectively mean hydrogen or a protective group].

In this specification, amino acids and peptides are designated either by the abbreviations commonly used in the art or by those adopted by the Committee on Chemical Nomenclature of IUPAC-IUB. Some of such abbreviations are as follows.

Ala: alanine
Gly: glycine
Leu: leucine
Phe: phenylalanine
MePhe: N-methyl-phenylalanine
Tyr: tyrosine
MeTyr: N-methyl-tyrosine
Gln: glutamine
Thr: threonine
Ser: serine
Nva: norvaline
Met(O): methionine sulfoxide
Met($O_2$): methionine sulfone
Lys: lysine
His: histidine
Glu: glutamic acid In the following description, the compounds repeatedly referred to are designated by the following abbreviations.

DCC: N,N'-dicyclohexylcarbodiimide
HONB: N-hydroxy-5-norbornene-2,3-dicarboximide
ONB: HONB ester
Z: benzyloxycarbonyl
OEt: ethyl ester
ONP: p-nitrophenyl ester
Tos: tosyl
BOC: t-butoxycarbonyl
$Bu^t$: t-butyl
DMF: dimethylformamide
Bzl: benzyl
HOBT: N-hydroxybenzotriazole
MeOH: methyl alcohol
AcOEt: ethyl acetate
TEA: triethylamine
THF: tetrahydrofuran
TFA: trifluoro acetic acid
DCHA: dicyclohexylamine
$OCH_3$: methylester
Cl-Z: p-chlorobenzyloxycarbonyl Throughout this specification, wherever any amino acid or its residue is designated by an abbreviation in the above manner, it represents the L-form thereof unless otherwise specified, while the D-form of any amino acid or residue thereof is specified by (D)- or D-.

Referring, now, to the above general formulas (I) and (II), the lower alkyl $R_1$ is preferably a straight-chain or branched alkyl group of 1 to 6 carbon atoms, such as methyl, ethyl, propyl, isopropyl, n-butyl, isobutyl, sec-butyl, tert-butyl, n-pentyl, isopentyl, sec-amyl, tert-amyl, n-hexyl, isohexyl, 3-methylpentyl, neohexyl and 2,3-dimethylbutyl.

The side chain of D-α-amino acid is represented by $R_2$ or $R_2'$ is the side chain of any of such amino acids as D-leucine, D-alanine, D-methionine, D-methioninesulfoxide, D-serine, D-threonine, D-phenylalanine, D-histidine, D-tryptophan, D-tyrosine, D-methioninesulfone, D-glutamine, D-asparagine, D-arginine, D-lysine, D-ornithine, D-glutamic acid, D-aspartic acid, D-cysteine, S-methyl-D-cysteine, S-ethyl-D-cysteine, S-methyl-D-cysteinesulfoxide, S-ethyl-D-cysteinesulfoxide, D-α-aminobutyric acid, D-valine, D-norvaline, D-norleucine, D-isoleucine and S-methyl-D-methionine.

In this context the side chain of D-α-amino acid includes the amino acids mentioned above having protective group such as tertiary butyl, benzyl, acetyl, formyl, benzyloxycarbonyl, p-chlorobenzyloxycarbonyl, p-methoxybenzyloxycarbonyl, t-butoxycarbonyl, t-amyloxycarbonyl, p-nitrobenzyloxy, t-butoxy, methoxy, ethoxy and benzyloxy.

The lower alkyl $R_3$ is preferably an alkyl group of 1 or 2 carbon atoms, such as methyl and ethyl.

The saturated or unsaturated and straight or branched lower aliphatic acyl group $R_4$ is preferably a group of 1 to 8 carbon atoms, and $R_4$ being particularly preferred is a group of 2 to 6 or 3 to 5 carbon atoms.

The examples of the saturated and straight or branched lower aliphatic acyl groups are formyl, acetyl, propionyl, isopropionyl, n-butyryl, isobutyryl, n-valeryl, isovaleryl hexanoyl, isohexanoyl, heptanoyl and octanoyl, as a parent acyl group.

The examples of the unsaturated and straight or branched lower aliphatic acyl groups are crotonoyl, methacryl and acryl, as a parent acyl group.

As examples of the halogen atom which may be present as a substitutent on acyl groups mentioned above, there may be mentioned chlorine, fluorine or bromine, for instance. The lower alkoxy which may substitute the acyl groups is preferably an alkoxy group of 1 to 4 carbon atoms, such as methoxy, ethoxy, n-propoxy, isopropoxy, n-butoxy, isobutoxy, tert-butoxy, etc. Particularly desirable are methoxy, ethoxy and n-propoxy.

The lower alkylthio which may substitute the acyl groups is preferably an alkylthio group of 1 to 4 carbon atoms, such as methylthio, ethylthio, n-propylthio, isopropylthio, n-butylthio, isobutylthio and tert-butylthio. Particularly desirable are methylthio, ethylthio, n-butylthio and isobutylthio.

The lower alkylthiooxide which may substitute the acyl group is preferably an alkylthiooxide group of 1 to 4 carbon atoms, such as methylthiooxide, ethylthiooxide, n-propylthiooxide, isopropylthiooxide, n-butylthiooxide, isobutylthiooxide and tert-butylthiooxide. Particularly desirable are methylthiooxide, ethylthiooxide, n-butylthiooxide and isobutylthiooxide.

The typical examples of substituted acyl group $R_4$ are hydroxyacetyl, 2-hydroxypropionyl, 3-hydroxypropionyl, 2-hydroxybutyryl, 3-hydroxybutyryl, 4-hydroxybutyryl, 2,3-dihydroxypropionyl, aminoacetyl, 2-aminopropionyl, 3-aminopropionyl, 4-aminobutyryl, ethoxyformyl, methoxyacetyl, 3-methoxypropionyl, 3-ethoxypropionyl, 4-methoxybutyryl, chloroacetyl, dichloroacetyl, 2-chloropropionyl, 3-chloropropionyl, 2,3-dichloropropionyl, 2-chlorobutyryl, 3-chlorobutyryl, 4-chlorobutyryl, 3-oxobutyryl, 3-oxovaleryl, 4-oxovaleryl, methylthioacetyl, 3-methylthiopropionyl, ethylthioacetyl, 3-ethylthiopropionyl, methylthiooxideacetyl, 3-methylthiooxidepropionyl, ethylthiooxideacetyl and 3-ethylthiooxidepropionyl.

As examples of the protective group $Y_1$ in the above general formula, there may be mentioned benzyloxycarbonyl, t-butoxycarbonyl, t-amyloxycarbonyl, isobornyloxycarbonyl, adamantyloxycarbonyl, chloro- or nitro-substituted benzyloxycarbonyl, o-phenylthio and diphenylphosphinomethyl.

The protective group $Y_2$ may for example be benzyl and t-butyl.

As regards the protective groups on $R_2'$ and $R_4'$, the protective group for protecting the hydroxy and/or carboxyl group of each parent group may for example be one of the groups mentioned for $Y_2$ and the protective group for the amino group of each parent group may for example be one of those mentioned for $Y_1$. The protective group $Y_3$ may be one of those protective groups mentioned for $Y_1$.

A tetrapeptide hydrazide derivative of chemical structural formula (I) is produced by condensing N-terminal amino acid or a peptide fragment of tetrapeptidehydrazide (I), having a N-terminal amino acid, with the remaining part of the tetrapeptidehydrazide (I). Thus, for example, the following alternative methods may be utilized for this purpose. The methods described in M. Bodansky and M. A. Ondetti: Peptide Synthesis, Interscience, New York, 1966; F. M. Finn and K. Hofman: The Proteins, Vol. 2, ed. by H. Nenrath, R. L. Hill, Academic Press Inc., New York, 1976; or Nobuo Izumiya et al; Peptide Gosei (Peptide Synthesis), Maruzen Inc., 1975, may be utilized. Thus, for example, the azide method, chloride method, acid anhydride method, mixed acid anhydride method, DCC method, active ester method, the method involving the use of Woodward's reagent K, carbodiimidazole method, reduction-oxidation method and DCC/HONB method may be mentioned. There are cases in which the NCA (N-carboxy-anhydride) method (the method involving the use of an intramolecular cyclic carbonyl compound corresponding to the amino acid without use of a protective group) may be utilized.

Prior to the condensation reaction, the carboxyl or-/and amino group in starting material which will not be pertinent to the reaction may be previously protected or the carboxyl or and amino groups of starting material which are pertinent to the reaction may be previously activated.

The protective groups for the starting material may be the protective groups mentioned hereinbefore. The carboxyl group of the starting material may also be protected in the form of metal salt (e.g. sodium salt, potassium salt), t-alkylamine salt (e.g. triethylamine salt, N-methylmorpholine salt) or ester (e.g. methyl ester, ethyl ester, benzyl ester, n-nitrobenzyl ester, t-butyl ester, t-amyl ester). As examples of the protective group for the amino group in the starting material, there may be mentioned benzyloxycarbonyl, t-butoxycarbonyl and isobornyloxycarbonyl. The imino group of histidine may be protected by benzyl, tosyl, 2,4-dinitrophenyl, t-butyloxycarbonyl and carbobenzoxy. The hydroxy group of tyrosine may be protected in the ether form by benzyl and t-butyl. The guanidino group of arginine may be protected by nitro, tosyl, carbobenzoxy, isobornyloxycarbonyl and adamantyloxycarbonyl.

As examples of the activated form of the carboxyl group in the starting material, there may be mentioned the corresponding acid anhydride, azide, active ester [i.e. esters with alcohols (e.g. pentachlorophenol, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide, N-hydroxybenzotriazole)]. As an example of the activated form of the amino group in the starting material, there may be mentioned the corresponding phosphoric acid amide.

Assuming that the starting materials are A and B, the above combinations of carboxyl and amino groups in starting materials may be as shown in the following table.

| Combination example | Starting materials | | | |
|---|---|---|---|---|
| | A | | B | |
| | COOH | NH$_2$ | COOH | NH$_2$ |
| 1* | Free | Protected | Protected | Free |
| 2 | Activated | Protected | Free | Free |
| 3 | Free | Protected | Protected | Activated |

Note:
In the case of *, a dehydrating agent (e.g. a carbodiimide reagent such as dicyclohexylcarbodiimide) is desirably present in the reaction system.

The reaction may be carried out in a solvent. This solvent is selected from among the solvents hitherto-known to be suited for peptide synthesis reactions. Thus, for example, there may be mentioned anhydrous or aqueous dimethylformamide, dimethylsulfoxide, pyridine, chloroform, dioxane, dichloromethane and tetrahydrofuran as well as appropriate mixtures of such solvents.

The reaction temperature is selected from the range hitherto-known to be suited for peptide synthesis reactions and may normally range from about $-20°$ C. to about 30° C. The precursor compounds (protected peptides) for the compounds of this invention may be easily produced as well by the solid-phase synthesis procedure.

The protected compound of formula (II) so obtained is subjected to a deprotecting reaction by which the protective groups are removed. While the deprotecting reaction depends on the type of protective group involved, it is preferred for commercial purposes that this reaction is such that it removes all the protective groups in a single step without affecting the peptide bonds. Thus, protective groups are chosen in consideration of this possibility. Table 1 shows some combinations of different types of protective groups and typical deprotecting conditions.

TABLE 1

| Conditions of removal | Protective group | | | | |
|---|---|---|---|---|---|
| | Y$_1$ | Y$_2$ | Protective group on R$_2'$ | Protective group on R$_4'$ | Y$_3$ |
| H$_2$/catalyst | Z | Bzl | — | — | Z |
| H$_2$/catalyst | Z | — | — | — | — |
| CF$_3$COOH | BOC | Bu$^t$ | Bu$^t$ | Bu$^t$ | BOC |
| 2N-HCl | BOC | — | — | — | — |
| (in acetic acid) | BOC | — | — | — | BOC |
| CH$_3$SO$_3$H | Z | — | — | — | BOC |

While Table 1 is a listing of some deprotecting reactions such as catalytic reduction involving the use of palladium black, palladium-on-carbon, platinum or the like catalyst and acid hydrolysis with trifluoroacetic acid, dilute hydrochloric acid or methanesulfonic acid, such other processes as reduction with sodium metal in liquid ammonia and acid hydrolysis with the use of trifluoromethanesulfonic acid, a solution of hydrogen bromide in glacial acetic acid, hydrogen fluoride or the like may also be mentioned. These reactions are generally conducted at suitable temperatures from $-20°$ C. to 40° C., and in the case of acid hydrolysis, the addition of a cation acceptor such as anisole, phenol or thioanisole is advantageous.

When the compound (I) is desired to have D-methionine sulfoxide as D-α-amino acid component, the required introduction of oxide may be conducted on any intermediary compound containing methionine residue in the course of peptide synthesis of this invention.

For example, (1) D-methionine sulfoxide is used as the starting material, (2) an intermediate of the compound (III) representable by the formula (III)

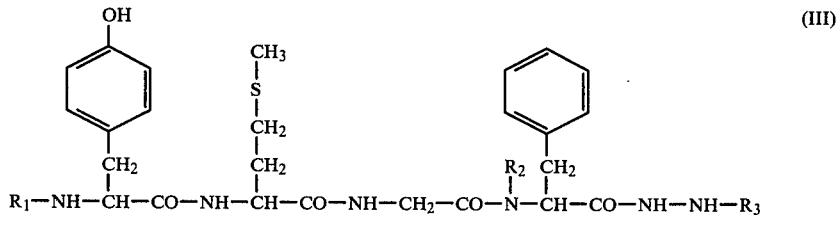

(D)

[wherein R$_1$, R$_2$ and R$_3$ have the same meaning as defined above] is oxidized, and then the resulting compound is subjected to peptide synthesis, or (3) the compound (III) is subjected to oxidation.

As examples of the oxidizing agent usable for the oxidation, there may be mentioned hydrogen peroxide, sodium perchloride, sodium perborate, chloramine T, tribromocresol, N-chlorosuccinimide and chloroauric acid.

The amount of the oxidizing agent is usually not less than about 1 equivalent, preferably about 1 to 10 equivalent to the compound (III).

The solvent usable for the reaction is, for example, water, acetic acid, alcohol (e.g. methylalcohol, ethylalcohol), or mixtures thereof.

The reaction temperature is generally $-20°$ C. to 40° C.

Aster completion of the reaction, the peptide derivative (I) so produced is isolated by procedures which are known for the separation of peptide derivatives, i.e. by extraction, distribution, reprecipitation, recrystallization or column chromatography.

The peptide (I) may be obtained in the form of a salt, e.g. the organic acid salt or inorganic acid salt, preferably acetate, citrate, tartrate, hydrochloride or sulfate.

The following is the result of a pharmacological test with the compound (I) of this invention.

Hot-plate test

Ta:CF$_1$ mice, 4 weeks old and with body weights 18-22 g, were used. When the animal is placed on a hot copper plate maintained at 55°±0.5° C., it shows certain responses to the thermal stimulus such as licking the soles of the hind paws or jumping up to escape. The mice showing such responses within 20 seconds after placement on the hot plate were selected into groups of 10 animals. The test drug was injected intravenously or subcutaneously, and after 5, 10, 20, 30, 45 and 60 minutes, their response times were measured and compared with the response times of untreated animals (control groups). To avoid irreversible injuries to the soles, 60 seconds was selected as the maximum test time. The indexes of analgesic action (response prolongation rate, %) were derived by means of the following equation and a t-test was carried out to evaluate the effectiveness of the test drug.

$$\frac{\text{Response time after dosing (sec.)} - \text{Response time before dosing (sec.)}}{60 - \text{response time before dosing (sec.)}} \times 100$$

In the above test, the compound (I) of this invention in doses of no more than 2 mg/kg preferably 1 mg/kg or 200 μg/kg displayed analgesic actions equivalent to a prolongation rate of not less than 40% with a peak occurring at 5 to 60 minutes preferably 5 to 30 or 5 to 20 minutes and some particularly effective kinds of compound (I) displayed marked pain reliefs even in small doses not exceeding 0.5 mg/kg preferably not exceeding 0.1 mg/kg or not exceeding 20 μg/kg.

As mentioned hereinbefore, the compound (I) according to this invention produces a definite analgesic action, as evidenced by results of hot-plate tests in mice, at the dose levels between about 0.05 to 10 mg, preferably about 0.05 mg to about 2 mg/kg, or about 0.2 to 1 mg/kg and in view of its superior efficacy as compared with β-endorphine, is of value as an analgesic drug.

Therefore, the compound (I) and its pharmacologically acceptable acid addition salts can for instance be used as analgesics for the relief of pains inclusive of the pain of advanced-stage cancer and as medicaments for the treatment of gastrointestinal disorders such as diarrhea, in mammalian animals such as mouse, rat, rabbit, dog, monkey, human being or be used as a medicaments for the treatment of mental disease.

The compound (I) and its acid addition salts thereof, which are provided by this invention, are extremely low in toxicity and no death is encountered even at 200 mg/kg which is by far beyond the effective dose.

The compound of this invention may be administered in its free form or as an acid addition salt thereof. In the case of free compound (I), the proper dosage is generally in the range of 0.01 to 50 mg/kg, preferably 0.05 mg to 30 mg/kg or 0.1 to 20 mg/kg. The dosage of the acid addition salt of (I) may also range generally from 0.01 to 50 mg/kg, preferably 0.05 mg to 30 mg/kg or 0.1 to 20 mg/kg as free compound (I). The compound and salt according to this invention are mainly administered by routes other than the oral route (e.g. intravenous, subcutaneous, rectal), although they may be orally applied depending on condition. Particularly useful is continuous infusion or instillation in the course of a surgical operation.

Useful dosage forms include injections, suppositories, powders and so forth, although instillable preparations are also useful. Being stable substances, the compounds according to this invention can be stored as dissolved in physiological saline but they may be provided in the form of lyophilized ampoule preparations as compounded with mannitol or sorbitol for extemporaneous dissolution and use.

In the case of intravenous and subcutaneous injections, concentrations are preferably within the range of 1 to 25 mg/ml preferably 10 to 25 mg/ml or 10 to 20 mg/ml in physiological saline.

The present compound (I) also has activities of prolactin or growth hormone releasing activity, inhibitory effect on motor activity of small intestine and modulating of central nervous system.

There are some occasions that the present compound (II), which has a protective group, has a similar activity to those of the present compound (I).

The following examples are given to describe this invention in further detail. It should be understood that the Sephadex LH-20 used for the purification of final products is the product of Pharmacia (Sweden) and that the purity of each compound prepared was assayed by thin-layer chromatography on Kieselgel 60F-254, Merck, using the following solvent systems:

$R_f^1$: chloroform-methanol-acetic acid (9:1:0.5)

$R_f^2$: ethyl acetate-pyridine-acetic acid-water (60:20:6:10)

$R_f^3$: n-butanol-acetic acid-water (4:1:1)

REFERENCE EXAMPLE 1

Production of Z-Tyr-(D)-Leu-Gly-OH (I) Production of Z-(D)-Leu-Gly-OH

In 20 ml of water is dissolved 3.3 g of glycine, and 3.4 g of sodium hydrogen carbonate is added. Then, under stirring, a solution (100 ml) of 17.0 g (40 m mols) of Z(D)-Leu-ONB in DMF is added. The mixture is stirred at room temperature overnight. Next morning the DMF is distilled off and 200 ml of AcOEt and 50 ml of 1 N-aqueous hydrochloric acid are added to the residue. The AcOEt layer is washed with water and dried over anhydrous sodium sulfate. The AcOEt is then distilled off and the residue is crystallized with petroleum ether. Recrystallization from AcOEt-petroleum ether yields 9.8 g (75%) of the above indicated compound. m.p. 110°–111° C.; $[\alpha]_D^{27}+24.3°$ (c=1.0, MeOH); $Rf^1=0.42$.

Elemental analysis, for $C_{16}H_{22}O_5N_2$: Calcd.: C, 59.61; H, 6.88; N, 8.69; Found: C, 59.59; H, 6.85; N, 8.74.

(II) Production of Z-Tyr-(D)-Leu-Gly-OH

In 100 ml of MeOH is dissolved 7.0 g (22 m mols) of Z-(D)-Leu-Gly-OH and catalytic reduction is carried out with palladium black as the catalyst. The catalyst is filtered off, the MeOH is distilled off and the residue is suspended in THF-water (100 ml–10 ml). The suspension is cooled and dissolved by the dropwise addition of 3 ml of TEA. To this solution is added 10.5 g of Z-Tyr-ONB and the mixture is stirred at room temperature overnight. The THF is distilled off and 200 ml of AcOEt and 25 ml of 1 N-aqueous hydrochloric acid are added to the residue. The AcOEt layer is washed with water and dried over anhydrous sodium sulfate. The AcOEt is then distilled off and the residue is treated with diethylether and recrystallized from AcOEt. 8.2 g (78%); m.p. 179°–181° C.; $[\alpha]_D^{27}+45.2°$ (c=0.5, MeOH); $Rf^1=0.38$ Elemental analysis, for $C_{25}H_{31}O_7N_3$: Calcd.: C, 61.68; H, 6.51; N, 8.64; Found: C, 61.84; H, 6.44; N, 8.66.

EXAMPLE 1

Production of H-Tyr-(D)-Leu-Gly-Phe-NH-NH$_2$ (I) Production of Z-Tyr-(D)-Leu-Gly-Phe-OMe In 50 ml of THF are dissolved 1.45 g of Z-Try-(D)-Leu-Gly-OH and 590 mg of HONB, and under cooling at 0° C., 680 mg of DCC is added and the mixture stirred for 4 hours. The by-product urea derivative is filtered off, 750 mg of H-Phe-OMe hydrochloride and 0.5 ml of TEA are added to the filtrate and the mixture is stirred at room temperature overnight. The THF is then distilled off, the residue is extracted with 100 ml of AcOEt and the extract is washed with 5% aqueous sodium hydrogen carbonate and dried over anhydrous sodium sulfate. The AcOEt is distilled off and the residue is purified by precipitation with petroleum ether and recrystallized from AcOEt-diethyl ether, 1.73 g (89%) m.p. 100°–101° C.; $[\alpha]_D^{22} -2.6°$ (c=0.5, DMF); $Rf^1 = 0.68$.

Elemental analysis, for $C_{35}H_{42}O_8N_4$: Calcd.: C, 65.00; H, 6.55; N, 8.66; Found: C, 64.97; H, 6.95; N, 8.62.

(II) Production of Z-Tyr-(D)-Leu-Gly-Phe-NH-NH$_2$

In 5 ml of DMF is added 517 mg of Z-Tyr-(D)-Leu-Gly-Phe-OMe, and after the addition of 0.1 ml of NH$_2$—NH$_2$. H$_2$O, the solution is allowed to stand at room temperature for 3 days. The DMF is then distilled off and the residue is treated with water, by filtration and purified by reprecipitation with MeOH-diethylether. 410 mg (80%); m.p. 176°–177° C. (decomp.); $[\alpha_D^{22} -22.7°$ C. (c=0.4, DMF); $Rf^1 = 0.20$ Elemental analysis, for $C_{34}H_{42}O_7N_6 \cdot \frac{1}{2}H_2O$: Calcd.: C, 62.27; H, 6.45; N, 12.82; Found: C, 62.03; H, 6.57; N, 12.64.

(III) Production of H-Tyr-(D)-Leu-Gly-Phe-NH-NH$_2$

In 50 ml of MeOH is dissolved 350 mg of Z-Tyr-(D)-Leu-Gly-Phe-NH-NH$_2$, and following addition of 0.1 ml of acetic acid, catalytic reduction is carried out with palladium black as the catalyst. The catalyst is filtered off, the filtrate is concentrated and the residue is dissolved in a small amount of 1N-aqueous acetic acid and put on a column of Sephadex LH-20(2.5×120 cm). Elution is carried out with 1 N-aqueous acetic acid and fractions from 320 through 340 ml are collected and lyophilized. 210 mg (60%); $[\alpha]_D^{22} +22.6°$ (c=0.38, MeOH); $Rf^2=0.34$; amino acid analysis (acid hydrolyzate): Gly, 1.00; Leu, 1.00; Tyr, 0.90; Phe, 1.02; mean recovery rate 70%.

EXAMPLE 2

Production of H-Tyr-(D)-Ala-Gly-Phe-NH-NH$_2$ (I) Production of Z-Tyr-(D)-Ala-Gly-OH In 200 ml of MeOH is dissolved 8.2 g of Z-(D)-Ala-Gly-OBu$^t$ and catalytic reduction is carried out with palladium black as the catalyst.

The catalyst is filtered off, the MeOH is distilled off and the residue is dissolved in 70 ml of trifluoroacetic acid and allowed to stand at room temperature for 40 minutes. The trifluoroacetic acid is distilled off and the residue is treated with diethyl ether and collected by filtration. The powders thus obtained are suspended in 50 ml of water and dissolved by the addition of 4.7 g of sodium hydrogen carbonate. To this solution is added 100 ml of a THF solution containing 13.3 g (28 m mols) of Z-Tyr-ONB and the mixture is stirred at room temperature overnight. The reaction mixture is neutralized with 1 N-HCl and extracted with 150 ml of AcOEt. The extract is washed with water and dried over anhydrous sodium sulfate. The AcOEt is distilled off and the residue is treated with diethyl ether, collected by filtration and recrystallized from AcOEt. 8.5 g (69%); m.p. 184°–185° C.; $[\alpha]_D^{22} +25.6°$ (c=0.5, MeOH); $Rf^1=0.16$.

Elemental analysis, for $C_{22}H_{25}O_7N_3$: Calcd.: C, 59.58; H, 5.68; N, 9.48; Found: C, 59.29; H, 5.81; N, 9.32.

(II) Production of Z-Phe-NHNH-BOC

In 100 ml of THF are dissolved 18.4 g of Z-Phe-ONB and 5.3 g of NH$_2$-NH-BOC. The solution is stirred at room temperature overnight. The THF is then distilled off, the residue is extracted with 150 ml of AcOEt and the extract is washed with aqueous citric acid and 5% aqueous sodium hydrogen carbonate, dried over Na$_2$SO$_4$ and distilled to remove the AcOEt. The residue is treated with petroleum ether, collected by filtration and recrystallized from AcOEt-petroleum ether. 13.2 g (80%); m.p. 107°–109° C.; $[\alpha]_D^{19} -23.4°$ (c=0.5, MeOH); $Rf^1=0.71$.

Elemental analysis, for $C_{22}H_{27}O_5N_3$: Calcd.: C, 63.90; H, 6.58; N, 10.16; Found: C, 64.18; H, 6.61; N, 9.88.

(III) Production of Z-Tyr-(D)-Ala-Gly-Phe-NH-NH-BOC

In 100 ml of MeOH is dissolved 3.6 g of Z-Phe-NH-NH-BOC, and following addition of 0.5 ml of acetic acid, catalytic reduction is carried out with palladium black as the catalyst. The catalyst is filtered off, 10 ml of DMF is added to the filtrate and the MeOH is distilled off. On the other hand, 3.5 g of Z-Tyr-(D)-Ala-Gly-OH and 1.56 g of HONB are dissolved in 50 ml of THF, and under cooling at 0° C., 1.80 g of DCC is added. The mixture is stirred at 0° C. for 6 hours. The insolubles are filtered off, the filtrate is combined with the amine component and the mixture is stirred at room temperature overnight. The THF is distilled off, the residue is extracted with 150 ml of AcOEt and the extract is washed with 5% aqueous sodium hydrogen carbonate and with aqueous citric acid, and dried over anhydrous sodium sulfate. The AcOEt is then distilled off and the residue is treated with petroleum ether and recrystallized from AcOEt-petroleum ether. 3.7 g (67%); m.p. 143°–146° C. (decomp.); $[\alpha]_D^{22} -25.4°$ (c=0.5, DMF); $Rf^1=0.38$.

Elemental analysis, for $C_{26}H_{44}O_9N_6$: Calcd.: C, 61.35; H, 6.29; N, 11.93; Found: C, 61.05; H, 6.42; N, 11.58.

(IV) Production of Z-Tyr-(D)-Ala-Gly-Phe-NH-NH$_2$

In 30 ml of trifluoroacetic acid is dissolved 3.5 g of Z-Tyr-(D)-Ala-Gly-Phe-NH-NH-BOC and the solution is allowed to stand at room temperature for 20 minutes. The trifluoroacetic acid is distilled off and the residue is treated with diethyl ether and collected by filtration. The resulting powders are dissolved in 10 ml of DMF and stirred with 1.4 ml of TEA. The DMF is distilled off and the residue is treated with water, collected by filtration and purified by reprecipitation with methanol-diethylether. 2.8 g (96%); m.p. 182°–184° C. (decomp.); $[\alpha]_D^{22} -23.0°$ (c=0.5, DMF); $Rf^1=0.17$.

Elemental analysis, for $C_{31}H_{36}O_7N_6$: Calcd.: C, 61.58; H, 6.00; N, 13.90; Found: C, 61.32; H, 5.91; N, 13.72.

(V) Production of H-Tyr-(D)-Ala-Gly-Phe-NH-NH$_2$

In 50 ml of MeOH is dissolved 250 mg of Z-Tyr-(D)-Ala-Gly-Phe-NH-NH$_2$, and following addition of 0.1 ml of acetic acid, catalytic reduction is carried out with palladium black as the catalyst. The catalyst is filtered off, the filtrate is dissolved in a small amount of 1 N-aqueous acetic acid and the solution is put on a column of Sephadex LH-20(2.5×120 cm). Elution is carried out with 1 N-aqueous acetic acid and fractions from 310 ml through 335 ml are pooled and lyophilized. 95 mg (38%); $[\alpha]_D^{22}+20.5°$ (c=0.2, MeOH); $Rf^2=0.22$; amino acid analysis (hydrolyzed with HCl): Gly, 1.00; Ala, 1.05; Tyr, 0.89; Phe, 1.01; mean recovery rate 81%.

EXAMPLE 3

Production of
H-Tyr-(D)-Leu-Gly-Phe-NH-NH-CO-CH₃

(I) Production of Z-Phe-NH-NH-CO-CH₃

In 50 ml of THF is dissolved 2.03 g (6.5 m mols) of Z-Phe-NH-NH₂, and under cooling, 1.4 ml of acetic anhydride and 0.9 ml of TEA are added dropwise. The mixture is stirred at room temperature for 2 hours. The crystals are collected by filtration, washed with diethyl ether and recrystallized from AcOEt. 1.9 g (83%); m.p. 205°–206° C.; $[\alpha]_D^{23}-16.4°$ (c=0.5, DMF); $Rf^1=0.60$.

Elemental analysis, for $C_{20}H_{23}O_5N_3$: Calcd.: C, 62.32; H, 6.02; N, 10.90; Found: C, 62.38; H, 6.09; N, 10.49.

(II) Production of
Z-Tyr-(D)-Leu-Gly-Phe-NH-NH-CO-CH₃

In 50 ml of MeOH is dissolved 700 mg of Z-Phe-NH-NH-CO-CH₃, and following addition of 0.2 ml of acetic acid, catalytic reduction is carried out with palladium black as the catalyst. The catalyst is filtered off, the MeOH is distilled off and the residue is dissolved in 20 ml of THF. On the other hand, 680 mg (1.4 m mols) of Z-Tyr-(D)-Leu-Gly-OH and 300 mg of HONB are dissolved in 20 ml of THF, and after cooling, 330 mg of DCC is added and stirred at 0° C. for 5 hours. The insolubles are filtered off, the filtrate is combined with the amine component previously prepared and the mixture is stirred at room temperature overnight. The THF is distilled off and the residue is treated with AcOEt, collected by filtration and purified by reprecipitation with methanol-AcOEt, 0.71 g (74%); m.p. 184°–185° C.; $[\alpha]_D^{23}-13.4°$ (c=0.5, DMF); $Rf^1=0.28$.

Elemental analysis, for $C_{36}H_{44}O_8N_6$: Calcd.: C, 62.77; H, 6.44; N, 12.20; Found: C, 62.52; H, 6.81; N, 12.04.

(III) Production of
H-Tyr-(D)-Leu-Gly-Phe-NH-NH-CO-CH₃

In 50 ml of MeOH is dissolved 500 ml of Z-Tyr-(D)-Leu-Gly-Phe-NH-NH-CO-CH₃, and following addition of 1 ml of acetic acid, catalytic reduction is carried out with palladium black as the catalyst. The catalyst is filtered off, the solvent is distilled off, the residue is treated with water and the insolubles are filtered off. The filtrate is lyophilized and the resulting powders are put on a column of Sephadex LH-20 (2.5×120 cm).

Elution is carried out with 1 N-aqueous acetic acid and fractions from 320 ml through 345 ml are pooled and lyophilized. 245 mg (50%); $[\alpha]_D^{23}+26.7°$ (c=0.3, MeOH); $Rf^2=0.41$; amino acid analysis (hydrolyzed with HCl)- Gly, 1.00; Leu, 1.05; Tyr, 0.93; Phe, 1.02; mean recovery rate 82%.

EXAMPLE 4

Production of
H-Tyr-(D)-Ala-Gly-Phe-NH-NH-CO-(CH₂)₃-CH₃

(I) Production of
Z-Tyr-(D)-Ala-Gly-Phe-NH-NH-CO-(CH₂)₃-CH₃

In 5 ml of DMF are dissolved 604 mg (1 m mol) of Z-Tyr-(D)-Ala-Gly-Phe-NH-NH₂, 297 mg of HOBT and 0.2 ml of CH₃(CH₂)₃COOH. After cooling the solution to 0° C., 454 mg of DCC is added and the mixture is stirred at 0° C. for 4 hours and at room temperature overnight.

The insolubles are filtered off, the DMF is distilled off and the residue is extracted with 100 ml of AcOEt, washed with 5% aqueous sodium hydrogen carbonate and dried over anhydrous sodium sulfate. The AcOEt is distilled off and the gel residue is treated with diethyl ether, collected by filtration and purified by reprecipitation with methanol-AcOEt. 480 mg (70%); m.p. 178°–179° C.; $[\alpha]_D^{23}-22.4°$ (c=0.16, DMF); $Rf^1=0.46$.

Elemental analysis, for $C_{36}H_{44}O_8N_6$: Calcd.: C, 62.77; H, 6.44; N, 12.20; Found: C, 62.71; H, 6.77; N, 11.98.

(II) Production of
H-Tyr-(D)-Ala-Gly-Phe-NH-NH-CO-(CH₂)₃-CH₃

In 50 ml of MeOH is dissolved 430 mg of Z-Tyr-(D)-Ala-Gly-Phe-NH-NH-CO-(CH₂)₃-CH₃, and following addition of 1 ml of acetic acid, catalytic reduction is carried out with palladium black as the catalyst. The catalyst is filtered off, the MeOH is distilled off and the residue is dissolved in a small amount of 1 N-aqueous acetic acid and put on a column of Sephadex LH-20 (2.5×120 cm), elution being carried out with 1 N-aqueous acetic acid. The fractions from 325 ml through 340 ml are pooled and lyophilized. 240 mg (56%); $[\alpha]_D^{23}+24.5°$ (c=0.2, MeOH); $Rf^2=0.47$; amino acid analysis (hydrolyzed with HCl); Gly, 1.00; Ala, 0.95; Tyr, 0.88; Phe, 1.01; mean recovery rate 82%.

EXAMPLE 5

Production of
H-Tyr-(D)-Ala-Gly-Phe-NH-NH-CO-CH₂-CH(CH₃)₂

(I) Production of
Z-Tyr-(D)-Ala-Gly-Phe-NH-NH-CO-CH₂-CH(CH₃)₂

The procedure of Example 4-(I) is repeated except that 530 mg (0.88 m mol) of Z-Tyr-(D)-Ala-Gly-Phe-NH-NH₂ and 0.15 ml of (CH₃)₂CH-CH₂-COOH are employed. 320 mg (53%); m.p. 228°–230° C.; $[\alpha]_D^{23}-23.9°$ (c=0.28, DMF); $Rf^1=0.46$.

Elemental analysis, for $C_{36}H_{44}O_8N_6$: Calcd.: C, 62.77; H, 6.44; N, 12.20; Found: C, 62.58; H, 6.35; N, 11.95.

(II) Production of
H-Tyr-(D)-Ala-Gly-Phe-NH-NH-CO-CH₂-CH(CH₃)₂

The procedure of Example 4-(II) is repeated except that 170 mg of Z-Tyr-(D)-Ala-Gly-Phe-NH-NH-CO-CH₂-CH(CH₃)₂ is employed. 105 mg (62%); $[\alpha]_D^{23}+21.1°$ (c=0.18, MeOH); $Rf^2=0.49$; amino acid analysis (hydrolyzed with HCl); Gly, 1.00; Ala, 1.02; Tyr, 0.96; Phe, 1.02; mean recovery rate 80%.

EXAMPLE 6

Production of
H-Tyr-(D)-Ala-Gly-Phe-NH-NH-CO-(CH₂)₂-Cl (I) Production of
Z-Tyr-(D)-Ala-Gly-Phe-NH-NH-CO-(CH₂)₂-Cl The procedure of Example 4-(I) is repeated except that 513 mg (0.85 m mol) of Z-Tyr-(D)-Ala-Gly-Phe-NH-NH₂ and 120 mg of Cl-CH₂-CH₂-COOH are employed. 360 mg (59%); m.p. 169°–170° C.; $[\alpha]_D^{23}-21.1°$ (c=0.37, DMF)

Elemental analysis, for $C_{34}H_{39}O_8N_6\cdot Cl$: Calcd.: C, 58.74; H, 5.65; N, 12.09; Cl, 5.10; Found: C, 58.61; H, 5.59; N, 11.81; Cl, 4.92.

(II) Production of
H-Tyr-(D)-Ala-Gly-Phe-NH-NH-CO-(CH$_2$)$_2$-Cl

The procedure of Example 4-(II) is repeated except that 250 mg of Z-Tyr-(D)-Ala-Gly-Phe-NH-NH-CO-(CH$_2$)$_2$-Cl is employed. 150 mg (60%); $[\alpha]_D^{23}$+20.5° (c=0.2, MeOH); Rf$^2$=0.42; amino acid analysis (acid hydrolyzate): Gly, 1.01; Ala, 0.95; Tyr, 0.88; Phe, 0.98; mean recovery rate 79%.

EXAMPLE 7

Production of
H-Tyr-(D)-Ala-Gly-Phe-NH-NH-CO-CH$_2$-CH$_2$-OH (I) Production of
Z-Tyr-(D)-Ala-Gly-Phe-NH-NH-CO-CH$_2$-CH$_2$-OH The procedure of Example 4-(I) is repeated except that 540 mg of Z-Tyr-(D)-Ala-Gly-Phe-NH-NH$_2$ and 0.12 ml of HO-CH$_2$-CH$_2$-COOH are employed. 320 mg (53%); m.p. 178°–179° C.; $[\alpha]_D^{23}$−22.3° (c=0.3, DMF); Rf$^1$=0.10.

Elemental analysis, for C$_{34}$H$_{40}$O$_9$N$_6$: Calcd.: C, 60.34; H, 5.96; N, 12.42; Found: C, 59.98; H, 5.85; N, 12.18.

(II) Production of
H-Tyr-(D)-Ala-Gly-Phe-NH-NH-CO-CH$_2$-CH$_2$-OH

The procedure of Example 4-(II) is repeated except that 250 mg of Z-Tyr-(D)-Ala-Gly-Phe-NH-NH-CO-CH$_2$-CH$_2$-OH is employed. Yield 100 mg (40%); $[\alpha]_D^{23}$+19.5° (c=0.21, MeOH); Rf$^2$=0.32; amino acid analysis (acid hydrolyzate): Gly, 1.00; Ala, 1.05; Tyr, 0.92; Phe, 1.00; mean recovery rate 79%.

EXAMPLE 8

Production of
H-Tyr-(D)-Ala-Gly-Phe-NH-NH-CO-CH$_2$-CH$_3$ (I) Production of
Z-Tyr-(D)-Ala-Gly-Phe-NH-NH-CO-CH$_2$-CH$_3$ The procedure of Example 4-(I) is repeated except that 495 mg (0.82 m mol) of Z-Tyr-(D)-Ala-Gly-Phe-NH-NH$_2$ and 0.1 ml of CH$_3$-CH$_2$-COOH are employed. 350 mg (65%); m.p. 190°–191° C.; $[\alpha]_D^{23}$−20.5° (c=0.3, DMF); Rf$^1$=0.26.

Elemental analysis, for C$_{34}$H$_{40}$O$_8$N$_6$: Calcd.: C, 61.80; H, 6.10; N, 12.72; Found: C, 61.53; H, 6.02; N, 12.65.

(II) Production of
H-Tyr-(D)-Ala-Gly-Phe-NH-NH-CO-CH$_2$-CH$_3$

The procedure of Example 4-(II) is repeated except that 250 mg of Z-Tyr-(D)-Ala-Gly-Phe-NH-NH-CO-CH$_2$-CH$_3$ is employed. 130 mg (52%); $[\alpha]_D^{23}$+25.5° (c=0.23, MeOH); Rf$^2$=0.42; amino acid analysis (acid hydrolyzate): Gly, 1.00; Ala, 0.95; Phe, 1.01; Tyr, 0.95; mean recovery rate 81%.

EXAMPLE 9

Production of
H-Tyr-(D)-Ala-Gly-Phe-NH-NH-CO-CH$_2$-CH$_2$-NH$_2$ (I) Production of
Z-Tyr-(D)-Ala-Gly-Phe-NH-NH-CO-CH$_2$-CH$_2$-NH-Z.

In 10 ml of DMF are dissolved 495 mg (0.82 m mol) of Z-Tyr-(D)-Ala-Gly-Phe-NH-NH$_2$ and 390 mg of Z-$\beta$-Ala-ONB. After cooling the solution, 0.14 ml of TEA is added, and the mixture is stirred at room temperature overnight. The DMF is distilled off, the residue is extracted with 100 ml of AcOEt, washed with 5% aqueous sodium hydrogen carbonate and dried over anhydrous sodium sulfate. The AcOEt is distilled off and the residue is treated with diethylether, collected by filtration and purified by reprecipitation with methanol-AcOEt.; 370 mg (56%); m.p. 231°–233° C.; $[\alpha]_D^{23}$−21.5° (c=0.27, DMF); Rf$^1$=0.26

Elemental analysis, for C$_{42}$H$_{47}$O$_{10}$N$_7$: Calcd.: C, 62.28; H, 5.85; N, 12.10; Found: C, 61.99; H, 5.94; N, 11.95.

(II) Production of
H-Tyr-(D)-Ala-Gly-Phe-NH-NH-CO-CH$_2$-CH$_2$-NH$_2$

The procedure of Example 4-(II) is repeated except that 280 mg of Z-Tyr-(D)-Ala-Gly-Phe-NH-NH-CO-CH$_2$-CH$_2$-NH-Z is employed. 160 mg (61%); $[\alpha]_D^{23}$ + 16.7° (c=0.27, MeOH); Rf$^2$=0.07; amino acid analysis: Gly, 1.00; Ala, 0.95; $\beta$-Ala, 0.99; Tyr, 0.89; Phe, 1.00; mean recovery rate 79%.

EXAMPLE 10

Production of
H-Tyr-(D)-Ala-Gly-Phe-NH-NH-CO-(CH$_2$)$_2$-CH$_3$ (I) Production of Z—Phe—NH—NH—$\overset{\overset{\displaystyle O}{\|}}{C}$—CH$_2$—CH$_2$—CH$_3$ In 30 ml of DMF is dissolved 2.5 g (8 m mols) of Z-PHe-NH-NH$_2$, and under cooling, 0.9 ml of CH$_3$CH$_2$CH$_2$COCl and 1.1 ml of TEA are added. The mixture is stirred at room temperature for 5 hours. To this reaction mixture is added water and the resulting crystals are collected by filtration, dried and recrystallized from AcOEt-petroleum ether 2.6 g (85%); m.p. 150°–156° C.; $[\alpha]_D^{23}$−27.2° (c=0.5, MeOH), Rf$^1$=0.71

Elemental analysis, for C$_{21}$H$_{25}$O$_4$N$_3$: Calcd.: C, 65.46; H, 6.48; N, 10.87; Found: C, 65.78; H, 6.57; N, 10.96.

(II) Production of
Z-Tyr-(D)-Ala-Gly-Phe-NH-NH-CO-CH$_2$-CH$_2$-CH$_3$

In 50 ml of MeOH is dissolved 505 mg of Z-Phe-NH-NH-CO-CH$_2$-CH$_2$-CH$_3$ and catalytic reduction is carried out with palladium black as the catalyst. The catalyst is filtered off, the MeOH is distilled off and the residue is dissolved in 20 ml of THF. On the other hand, 530 mg of Z-Tyr-(D)-Ala-Gly-OH and 237 mg of HONB are dissolved in 50 ml of THF and under cooling at 0° C., 271 mg of DCC is added and the mixture is stirred at 0° C. for 4 hours. The by-product urea derivative is filtered off, the filtrate is combined with the amine component prepared above and the mixture is stirred at room temperature overnight.

The THF is then distilled off, the residue is extracted with 100 ml of AcOEt, and the extract is washed with 5% aqueous sodium hydrogen carbonate and dried over anhydrous sodium sulfate. The AcOEt is then distilled off and the residue is treated with diethyl ether, collected by filtration and purified by reprecipitation with AcOEt. 420 mg (50%); m.p. 203°–206° C.; $[\alpha]_D^{23}$−0.4°(c=0.5, MeOH); Rf$^1$=0.28.

Elemental analysis, for C$_{35}$H$_{42}$O$_8$N$_6$: Calcd. C, 62.30; H, 6.27; N, 12.46; Found C, 62.60; H, 6.52; N, 12.18.

(III) Production of
H-Tyr-(D)-Ala-Gly-Phe-NH-NH-CO-CH$_2$CH$_2$CH$_3$

In 50 ml of MeOH is dissolved 250 mg of Z-Tyr-(D)-Ala-Gly-Phe-NH-NH-CO-CH$_2$-CH$_2$-CH$_3$, and following addition of 0.2 ml of acetic acid, catalytic reduction is carried out with palladium black as the catalyst. The catalyst is filtered off, the filtrate is concentrated and the residue is dissolved in a small amount of 1N-aqueous acetic acid and put on a column of Sephadex LH-20(2.5×120 cm). Elution is carried out with 1 N-aqueous acetic acid and fractions from 320 ml through 340 ml are pooled and lyophilized. 110 mg(44%); $[\alpha]_D^{23}+23.2°$(c=0.25, MeOH); Rf$^2$=0.40; amino acid analysis (hydrolyzed with HCl): Gly, 1.06; Ala, 1.00; Tyr, 0.93; Phe, 0.93; mean recovery rate 90%.

EXAMPLE 11

Production of H-Tyr-(D)-Ala-Gly-Phe-NH-CO-OCH$_2$-CH$_3$ (I) Production of Z-Phe-NH-NH-CO-OCH$_2$-CH$_3$ The procedure of Example 10-(I) is repeated except that 1.8 g (5.7 m mols) of Z-Phe-NH-NH$_2$ and 0.7 ml of ethyl chlorocarbonate are employed. 1.5 g (69%); m.p.134° C.; $[\alpha]_D^{23}-20.6°$(c=0.5, DMF); Rf$^1$=0.69

Elemental analysis, for C$_{20}$H$_{23}$O$_5$N$_3$; Calcd.: C, 62.32; H, 6.02; N, 10.90; Found: C, 62.38; H, 6.09; N, 10.49.

(II) Production of
Z-Tyr-(D)-Ala-Gly-Phe-NH-NH-CO-OCH$_2$-CH$_3$

The procedure of Example 10-(II) is repeated except that 580 mg (1.3 m mols) of Z-Tyr-(D)-Ala-Gly-OH and 620 mg of Z-Phe-NH-NH-CO-OCH$_2$-CH$_3$ are employed to synthesize the indicated compound. 820 mg (93%); m.p.154°-155° C.; $[\alpha]_D^{23}-24.2°$ (c=0.45, DMF); Rf$^1$=0.40.

Elemental analysis, for C$_{34}$H$_{40}$O$_9$N$_6$: Calcd.: C, 60.34; H, 5.96; N, 12.42: Found: C, 60.09; H, 5.87; N, 12.21.

(III) Production of
H-Tyr-(D)-Ala-Gly-Phe-NH-NH-CO-OCH$_2$-CH$_3$

The procedure of Example 10-(III) is repeated except that 450 mg of Z-Tyr-(D)-Ala-Gly-Phe-NH-NH-CO-OCH$_2$-CH$_3$ is employed to synthesize the above-indicated compound. 240 mg (53%); $[\alpha]_D^{23}+18.1°$(c=0.2, MeOH); Rf$^2$=0.49; amino acid analysis: Gly, 1.00; Ala, 0.98; Tyr, 0.88; Phe, 1.02; mean recovery rate 78%.

EXAMPLE 12

Production of H-Tyr-(D)-Ala-Gly-MePhe-NH-NH$_2$ (I) Production of Z-Tyr-(D)-Ala-Gly-MePhe-OCH$_3$ In 20 ml of MeOH is dissolved 1.8 g (5.7 m mols) of Z-MePhe-OH, and following addition of 20 ml of 5N-HCl/ dioxane, the solution is allowed to stand at room temperature overnight. The solvent is distilled off and the residue is extracted with 100 ml of AcOEt, washed with water and dried over anhydrous sodium sulfate. The AcOEt is then distilled off, whereupon 1.5 g of oil is obtained. A 1.1 g portion of this oil is dissolved in 50 ml of MeOH and catalytic reduction is carried out with palladium black as the catalyst. The catalyst is filtered off, the MeOH is distilled off and the residue is dissolved in 20 ml of DMF. To this solution are added 1.55 g (3.5 m mols) of Z-Tyr-(D)-Ala-Gly-OH and 0.75 g of HONB, and under cooling at 0° C., 0.80 g of DCC is added. The mixture is stirred at 0° C. for 5 hours and at room temperature overnight. The by-product urea derivative is filtered off and the DMF is distilled off. The residue is extracted with 100 ml of AcOEt, washed with 5% aqueous sodium hydrogen carbonate and dried over anhydrous sodium sulfate. The AcOEt is distilled off and the residue is treated with diethyl ether and purified by reprecipitation with MeOH-diethylether. 1.2 g (56%); m.p.103°-104° C.; $[\alpha]_D^{23}-17.2°$(c=0.31; MeOH); Rf$^1$=0.68.

Elemental analysis, for C$_{33}$H$_{38}$O$_8$N$_4$ Calcd.: C, 64.06; H, 6.19; N, 9.06; Found: C, 63.91; H, 6.05; N, 8.89.

(II) Production of
Z-Tyr-(D)-Ala-Gly-MePhe-NH-NH$_2$

In the same manner as Example 1-(II), 1.0 g (1.6 m mols) of Z-Tyr-(D)-Ala-Gly-MePhe-OCH$_3$ is treated with 0.5 ml of NH$_2$-NH$_2$H$_2$O, whereby the above-indicated compound is obtained. 820 mg (82%); m.p.95°-96° C. (decomp.); $[\alpha]_D^{23}-26.8°$(c=0.5, DMF); Rf$^1$=0.29.

Elemental analysis, for C$_{32}$H$_{38}$O$_7$N$_6$; Calcd.: C, 62.12; H, 6.19; N, 13.59; Found: C, 61.85; H, 6.28; N, 13.09.

(III) Production of
H-Tyr-(D)-Ala-Gly-MePhe-NH-NH$_2$ 300 mg of Z-Tyr-(D)-Ala-Gly- MePhe-NH-NH$_2$ is treated in the same manner as Example 4-(II) to obtain the above-indicated compound. 155 mg (52%); $[\alpha]_D^{23}+12.0°$(c=0.2, MeOH); Rf$^2$=0.46; amino acid analysis (acid hydrolyzate): Gly, 1.00; Ala, 0.98; Tyr, 0.91; mean recovery rate 79%.

EXAMPLE 13

Production of
H-Tyr-(D)-Ala-Gly-Phe-NHNH-COCH$_2$-CH$_2$-CH$_2$-Cl (I) Production of Z-Phe-NHNH-COCH$_2$-CH$_2$-CH$_2$-Cl In 40 ml of DMF are dissolved 3.13 g (10 m mols) of Z-Phe-NHNH$_2$ and 1.27 g (10 m mols) of γ-chlorobutyric acid, and under cooling at 0° C., 2.2 g of DCC is added. The mixture is stirred at room temperature for 20 hours. The reaction mixture is filtered and concentrated under reduced pressure. The residue is dissolved in 150 ml of ethyl acetate, washed with water, 1 N-HCl and 4% sodium hydrogen carbonate in that order. It is then dried over anhydrous sodium sulfate, concentrated to dryness under reduced pressure and crystallized from ethyl acetate-petroleum ether. By the above procedure are obtained 3.6 g of needles (85.7%) melting at 185°-186° C.; Rf$^1$=0.32.

Elemental analysis, for C$_{21}$H$_{24}$O$_4$N$_2$Cl: Calcd.: C, 60.35; H, 5.79; N, 10.06; Cl, 8.49; Found: C, 60.51; H, 5.60; N, 10.15; Cl, 8.27.

(II) Production of
H-Tyr-(D)-Ala-Gly-Phe-NHNH-COCH$_2$CH$_2$CH$_2$.Cl

In 50 ml of methanol, 420 mg of Z-Phe-NHNHCOCH$_2$-CH$_2$-CH$_2$-Cl is catalytically reduced using palladium black as the catalyst. The catalyst is filtered off and the filtrate is concentrated to dryness. This residue and 445 mg of Z-Tyr-(D)-Ala-Gly-OH are dissolved in 10 ml of DMF, followed by addition of 180 mg of HONB. Then, under cooling at 0° C., 250 mg of DCC is added. The mixture is stirred at 0° C. for 3 hours and at room temperature for 12 hours. The insolubles are filtered off, the DMF is distilled off under reduced pressure and the residue is dissolved in 100 ml of a 1:2 mixture of n-butanol and ethyl acetate. The solution is washed with 1 N-HCl, 4% aqueous sodium hydrogen carbonate and water in the order mentioned. The solvent is then distilled off under reduced pressure and the residue is dissolved in 50 ml of methanol. After addition of 1 ml of glacial acetic acid, catalytic reduction is carried out with palladium black as the catalyst. The catalyst is filtered off, the filtrate is concentrated to dryness under reduced pressure and the residue is dissolved in 10 ml of 1 N-aqueous acetic acid. The insolubles are filtered off and the filtrate is run onto a column of Sephadex LH-20 (3×45 cm), elution being carried out with 1 N-aqueous acetic acid. As in the fractions from 215 ml to 236 ml the desired product is eluted, the fractions are pooled and lyophilized to obtain 360 mg of the indicated compound. $Rf^2 = 0.485$; $[\alpha]_D^{23} + 18.2°(c=0.28, MeOH)$; amino acid analysis: Gly, 1.00; Ala, 1.02; Tyr, 0.89; Phe, 1.00; mean recovery rate 78%.

EXAMPLE 14

Production of
H-Tyr-(D)-Ala-Gly-MePhe-NH-NH-CO-CH$_2$-CH$_3$ (I) Preparation of
Z-Tyr-(D)-Ala-Gly-MePhe-NH-NH-CO-CH$_2$-CH$_3$ In 5 ml of DMF are dissolved 426 mg of Z-Tyr-(D)-Ala-Gly-MePhe-NH-NH$_2$ and 0.07 ml of propionic acid, and under cooling at 0° C., 130 mg of HOBT and 200 mg of DCC are added. The mixture is stirred at 0° C. for 5 hours and at room temperature overnight. The insolubles are filtered off, the DMF is distilled off and the residue is extracted with 50 ml of AcOEt, washed with water and dried over anhydrous sodium sulfate. The AcOEt is distilled off and the residue is treated with diethyl ether and collected by filtration. Yield 410 mg (87%), m.p.139°-141° C., $Rf^1 = 0.35$; $[\alpha]_D^{24} - 32.0°(c=0.43, DMF)$, Elemental analysis, for C$_{35}$H$_{42}$O$_8$N$_6$: Calcd.: C, 57.68; H, 6.63; N, 11.53; Found: C, 57.55; H, 6.42; N, 11.33.

(II) Preparation of
H-Tyr-(D)-Ala-Gly-MePhe-NH-NH-CO-CH$_2$-CH$_3$

In 50 ml of MeOH is dissolved 250 mg of Z-Tyr-(D)-Ala-Gly-MePhe-NH-NH-CO-CH$_2$-CH$_3$ and catalytic reduction is carried out with palladium black as the catalyst. The catalyst is filtered off, the MeOH is distilled off, the residue is dissolved in 50 ml of water and the insolubles are filtered off, followed by lyophilization. The resultant powder is dissolved in a small amount of N-aqueous acetic acid and put on a column of Sephadex LH-20(2.5×120 cm), elution being carried out with 1 N-aqueous acetic acid. The fractions from 290 ml to 315 ml are collected and lyophilized to recover 100 mg of the above-indicated compound. $Rf^2 = 0.47$; $[\alpha]_D^{24} - 7.7°(c=0.16, MeOH)$; amino acid analysis: Gly, 1.00; Ala, 1.03; Tyr, 0.92; mean recovery rate 81%.

EXAMPLE 15

Production of
H-Tyr-(D)-Ala-Gly-MePhe-NH-NH-CO-CH$_2$-CH$_2$-CH$_3$ (I) Preparation of
Z-Tyr-(D)-Ala-Gly-MePhe-NH-NH-CO-CH$_2$-CH$_2$-CH$_3$ Using 426 mg of Z-Tyr-(D)-Ala-Gly-MePhe-NH-NH$_2$ and 0.08 ml of n-butyric acid, the procedure of Example 14-(I) was followed to obtain 395 mg of the indicated compound (83%). m.p.135°-137° C.; $Rf^1 = 0.37$; $[\alpha]_D^{25} - 31.5°(c=0.3, DMF)$;

Elemental analysis, for C$_{36}$H$_{44}$O$_8$N$_6$: Calcd.: C, 62.77; H, 6.44; N, 12.20; Found: C, 62.48; H, 6.31; N, 11.95.

(II) Production of
H-Tyr-(D)-Ala-Gly-MePhe-NH-NH-CO-CH$_2$-CH$_2$-CH$_3$

By the same procedure as Example 14-(II), 250 mg of Z-Tyr-(D)-Ala-Gly-MePhe-NH-NH-CO-CH$_2$-CH$_2$-CH$_3$ is deprotected and purified to obtain 110 mg of the indicated compound. $Rf^2 = 0.48$; $[\alpha]_D^{25} - 7.2°(c=0.2, MeOH)$, amino acid analysis: Gly, 1.00; Ala, 0.98; Tyr, 0.86; mean recovery rate 83%.

EXAMPLE 16

Production of
H-Tyr-(D)-Ala-Gly-MePhe-NH-NH-CO-CH$_2$-CH$_2$-CO-CH$_3$

Using 482 mg of Z-Tyr-(D)-Ala-Gly-MePhe-NH-NH$_2$ and 0.13 ml of 4-oxo-n-valeric acid, the procedure of Example 14-(I) is followed to obtain the above-indicated compound, 390 mg (70%); m.p.139°-140° C.; $Rf^1 = 0.49$; $[\alpha]_D^{24} - 27.6°(c=0.27, DMF)$;

Elemental analysis, for C$_{37}$H$_{44}$O$_9$N$_6$.H$_2$O: Calcd.: C, 60.48; H, 6.31; N, 11.44; Found: C, 60.19; H, 6.25; N, 11.28.

(II) Production of
H-Tyr-(D)-Ala-Gly-MePhe-NH-NH-CO-CH$_2$-CH$_2$-CO-CH$_3$

Using 340 mg of Z-Tyr-(D)-Ala-Gly-MePhe-NH-NH-CO-CH$_2$-CH$_2$-CO-CH$_3$, the procedure of Example 14-(II) is followed to obtain 170 mg of the indicated compound. $Rf^2 = 0.49$; $[\alpha]_D^{24} - 6.0°(c=0.3, MeOH)$, amino acid analysis: Gly, 1.00; Ala, 0.98; Tyr, 0.97; mean recovery rate 85%.

EXAMPLE 17

Production of
H-MeTyr-(D)-Ala-Gly-Phe-NH-NH-CO-CH$_2$-CH$_3$ (I) Preparation of Z-(D)-Ala-Gly-Phe-OEt In 20 ml of DMF are dissolved 0.90 g of Z-(D)-Ala-Gly-OH and 0.63 g of HONB and, under cooling at 0° C., 0.75 g of DCC is added. The mixture is stirred for 4 hours, at the end of which time the insolubles are filtered off.

To the filtrate are added 0.81 g of H-Phe-OEt·hydrochloride and 0.5 ml of TEA, followed by stirring at room temperature overnight. The solvent is distilled off, the residue is extracted with 100 ml of AcOEt and the extract is washed with 1 N-aqueous hydrochloric acid and with 5% aqueous sodium hydrogen carbonate and dried over anhydrous sodium sulfate. Removal of AcOEt by distillation leaves crystals, which are collected by filtration and recrystallized from AcOEt-petroleum ether. 1.2 g (83%); m.p.109°–110° C.; $Rf^1=0.78$; $[\alpha]_D^{27}+1.6°(c=0.44, DMF)$ Elemental analysis, for $C_{24}H_{29}O_6N_3$: Calcd.: C, 63.28; H, 6.42; N, 9.23; Found: C, 63.38; H, 6.47; N, 9.03.

(II) Production of Z-(D)-Ala-Gly-Phe-NHNH$_2$

In 50 ml of MeOH is dissolved 3.3 g of Z-(D)-Ala-Gly-Phe-OEt and after 1 ml of hydrazine hydrate is added, the solution is allowed to stand at room temperature for 2 days. It is then treated with diethyl ether, collected by filtration and recrystallized from ethanol. 3.0 g (94%); m.p. 196°–197° C; $Rf^1=0.34$; $[\alpha]_D^{27}+2.4°(c=0.37, DMF)$.

Elemental analysis, for $C_{22}H_{27}O_5N_5$: Calcd.: C, 59.85; H, 6.16; N, 15.86; Found: C, 59.62; H, 6.12; N, 16.13.

(III) Production of Z-(D)-Ala-Gly-Phe-NH-NH-CO-CH$_2$-CH$_3$

In 10 ml of DMF are dissolved 1.1 g of Z-(D)-Ala-Gly-Phe-NH-NH$_2$ and 0.22 ml of propionic acid, and after cooling to 0° C., 0.44 g of HOBT and 0.62 g of DCC are added.

The mixture is stirred at 0° C. for 4 hours and, then, at room temperature overnight. The insolubles are filtered off, the DMF is distilled off and the residue is extracted with 100 ml of AcOEt. The extract is washed with aqueous sodium hydrogen carbonate and dried over anhydrous sodium sulfate. The AcOEt is distilled off and the gel-like residue is collected by filtration. The powders are washed by boiling with AcOEt. 0.95 g (77%); m.p. 197°–198° C.; $Rf^1=0.46$, $[\alpha]_D^{27}+4.8°(c=0.27, DMF)$ Elemental analysis, for $C_{25}H_{31}O_6N_5$: Calcd.: C, 60.34; H, 6.28; N, 14.08; Found: C, 60.14; H, 6.36; N, 13.65.

(IV) Production of Z-MeTyr(Bu$^t$)-(D)-Ala-Gly-Phe-NH-NH-CO-CH$_2$-CH$_3$

In 50 ml of MeOH is dissolved 497 mg of Z-(D)-Ala-Gly-Phe-NH-NH-CO-CH$_2$-CH$_3$ and catalytic reduction is carried out with palladium black as the catalyst. The catalyst is filtered off, the MeOH is distilled off and the residue is dissolved in 10 ml of DMF. On the other hand, 385 mg of Z-MeTyr(Bu$^t$)-OH and 215 mg of HONB are dissolved in 10 ml of THF and, after cooling to 0° C., 227 mg of DCC is added. The mixture is stirred at 0° C. for 4 hours, at the end of which time the insolubles are filtered off, while the filtrate is combined with the DMF solution of amine component prepared above, followed by stirring at room temperature overnight. The solvent is distilled off, the residue is extracted with 100 ml of AcOEt and the extract is washed with 5% aqueous sodium hydrogen carbonate and dried over anhydrous sodium sulfate. The AcOEt is then distilled off and the gel-like residue is collected by filtration. 620 mg. (85%); m.p.143°–144° C.; $Rf^1=0.63$; $[\alpha]_D^{27}-43.7°(C=0.4, DMF)$ Elemental analysis, for $C_{39}H_{50}O_8N_6$: Calcd.: C, 64.09; H, 6.90; N, 11.50; Found: 64.33; H, 7.21; N, 11.40.

(V) Production of H-MeTyr-(D)-Ala-Gly-Phe-NH-NH-CO-CH$_2$-CH$_3$

In 50 ml of MeOH is dissolved 500 mg of Z-MeTyr-(D)-Ala-Gly-Phe-NH-NH-CO-CH$_2$- CH$_3$ and catalytic reduction is carried out with palladium black as the catalyst. The catalyst is filtered off, the filtrate is distilled and the residue is dissolved and in a small amount of 1 N-aqueous acetic acid. The solution is put on a column of Sephadex LH-20(2.5×120 cm) and elution is carried out with 1 N-aqueous acetic acid.

The fractions from 330 ml through 370 ml are pooled and lyophilized. 360 mg. A 200 mg portion of the lyophilizate is dissolved in 2 ml of trifluoroacetic acid and the solution is allowed to stand at room temperature for 30 minutes. The solvent is distilled off and the residue is dried, dissolved in 50 ml of water and put on a column of Amberlite IRA-410 (acetate-form, 2×6 cm). The eluate and washings are combined and lyophilized. 170 mg. This powdery product is dissolved in a small amount of 1 N-aqueous acetic acid. The solution is run onto a column of Sephadex LH-20 (2×120 cm), elution being carried out with 1 N-aqueous acetic acid. The fractions from 285 ml through 300 ml are pooled and lyophilized. 70 mg. $Rf^3=0.33$; $[\alpha]_D^{27}+32.8°(c=0.21, MeOH)$; amino acid analysis: Gly, 1.00; Ala, 0.92; Phe, 1.02; mean recovery rate 78%.

EXAMPLE 18

Production of H-MeTyr-(D)-Ala-Gly-MePhe-NH-NH-CO-CH$_2$-CH$_3$ (I) Synthesis of Z-(D)-Ala-Gly-MePhe-NH-NH$_2$ In 50 ml of MeOH is dissolved 1.1 g of Z-MePhe-OMe and catalytic reduction is carried out with palladium black as the catalyst. The catalyst is filtered off, the MeOH is distilled off and the residue is dissolved in 10 ml of DMF. On the other hand, 0.92 g of Z-(D)-Ala-Gly-OH and 0.71 g of HONB are dissolved in 10 ml of DMF and, under cooling at 0° C., 0.75 g of DCC is added. The mixture is stirred at 0° C. for 4 hours, after which time the insolubles are filtered off, while the filtrate is combined with the above amine component and stirred at room temperature overnight. The DMF is distilled off and the residue is extracted with 100 ml of AcOEt, washed with 5% aqueous sodium hydrogen carbonate and dried over anhydrous sodium sulfate. The AcOEt is distilled off, whereupon 2.5 g of oil is obtained. This oil is dissolved in 20 ml of MeOH and, following addition of 1.5 ml of hydrazine hydrate, the solution is allowed to stand at room temperature overnight. The MeOH is distilled off, the residue is extracted with 100 ml of AcOEt and the extract is washed with water and dried over anhydrous sodium sulfate. The AcOEt is distilled off and the residue is treated with diethyl ether and collected by filtration. 2.0 g (80%); m.p. 85°–87° C.; $Rf^1=0.55$.

Elemental analysis, for $C_{23}H_{29}O_5N_5$: Calcd.: C, 60.64; H, 6.42; N, 15.38; Found: C, 60.51; H, 6.55; N, 15.11.

(II) Production of Z-MeTyr(Bu$^t$)-(D)-Ala-Gly-MePhe-NH-NH-CO-CH$_2$-CH$_3$

In 20 ml of THF are dissolved 0.91 g of Z-(D)-Ala-Gly-MePhe-NH-NH$_2$ and 0.19 ml of propionic acid, and at 0° C., 0.38 g of HOBT and 0.45 g of DCC are added. The mixture is stirred at 0° C. for 4 hours and, then, at room temperature overnight. The insolubles are filtered off, the THF is distilled off and the residue is extracted with 100 ml of AcOEt, washed with an aqueous solution of sodium hydrogen carbonate and dried over anhydrous sodium sulfate.

The AcOEt is then distilled off, whereupon 1.0 g of oil is obtained. This oil is dissolved in 50 ml of MeOH and catalytic reduction is carried out with palladium black as the catalyst. The catalyst is filtered off, the MeOH is distilled off and the residue is dissolved in 10 ml of THF. On the other hand, 0.73 g of Z-MeTyr(Bu$^t$)OH and 0.41 g of HONB are dissolved in 10 ml of THF, and with cooling at 0° C., 0.43 g of DCC is added. The solution is stirred at 0° C. for 4 hours. The insolubles are filtered off and the filtrate is combined with the THF solution of amine component prepared above and stirred at room temperature overnight. The THF is distilled off, the residue is extracted with 100 ml of AcOEt and washed with 5% aqueous sodium hydrogen carbonate. After drying over anhydrous sodium sulfate, the AcOEt is distilled off and the residue is purified by precipitation with diethyl ether. 1.2 g (86%); m.p. 110°–112° C.; Rf$^1$=0.61; [α]$_D^{25}$−54.7°(c=0.45, DMF)

Elemental analysis, for C$_{40}$H$_{52}$O$_8$N$_6$: Calcd.: C, 64.50; H, 7.04; N, 11.28; Found: C, 64.25; H, 7.16; N, 11.35.

(III) Production of
H-MeTyr-(D)-Ala-Gly-MePhe-NH-NH-CO-CH$_2$-CH$_3$

In the same manner as Example 17-(V), 600 mg of Z-MeTyr(Bu$^t$)-(D)-Ala-Gly-MePhe-NH-NH-CO-CH$_2$-CH$_3$ is catalytically reduced, treated with TFA and purified by gel filtration and the desired product is collected. 150 mg; Rf$^2$=0.48; [α]$_D^{25}$+14.4°(c=0.25, MeOH); amino acid analysis: Gly, 1.00; Ala, 0.95; mean recovery rate 81%

EXAMPLE 19

Production of
H-Tyr-(D)-Ala-Gly-MePhe-NH-NH-CO-CH$_3$ (I) Production of
Z-Tyr-(D)-Ala-Gly-MePhe-NH-NH-COCH$_3$ In the same manner as Example 14-(I), 426 mg of Z-Tyr-(D)-Ala-Gly-MePhe-NH-NH$_2$ and 0.06 ml of acetic acid are used to produce 405 mg of the indicated compound (85%). m.p.142°–143° C.; Rf$^1$=0.33; [α]$_D^{27}$−31.8°(c=0.4, DMF)

Elemental analysis, for C$_{34}$H$_{40}$O$_8$N$_6$: Calcd.: C, 61.80; H, 6.10; N, 12.72; Found: C, 61.65; H, 6.02 N, 12.66.

(II) Production of
H-Tyr-(D)-Ala-Gly-MePhe-NH-NH-CO-CH$_3$

In the same manner as Example 14-(II), 250 mg of Z-Tyr-(D)-Ala-Gly-MePhe-NH-NH-CO-CH$_3$ is deprotected and purified to obtain 130 mg of the indicated compound. Rf$^2$=0.44; [α]$_D^{25}$-6.9°(c=0.3, MeOH); amino acid analysis: Gly, 1.00; Ala, 0.99, Tyr, 0.92; mean recovery rate 82%.

Example 20

Production of
H-Tyr-(D)-Ala-Gly-MePhe-NH-NH-CO-CH$_2$-CH$_2$-O-CH$_2$-CH$_3$ (I) Production of
Z-Tyr-(D)-Ala-Gly-MePhe-NH-NH-CO-CH$_2$-CH$_2$-O-CH$_2$-CH$_3$ Using 358 mg of Z-Tyr-(D)-Ala-Gly-MePhe-NH-NH$_2$ and 0.08 ml of β-ethoxypropionic acid, the procedure of Example 14-(I) is repeated to obtain 300 mg of the above-indicated compound (73%); m.p.122°–124° C.; Rf$^1$=0.39; [α]$_D^{25}$−31.6°(c=0.24, DMF)

Elemental analysis, for C$_{37}$H$_{44}$O$_9$N$_6$: Calcd.: C, 62.00; H, 6.19; N, 11.72; Found: C, 61.73; H, 6.24; N, 11.58.

(II) Production of
H-Tyr-(D)-Ala-Gly-MePhe-NH-NH-CO-CH$_2$CH$_2$-O-CH$_2$-CH$_3$ In the same manner as Example 14-(II), 150 mg of Z-Tyr-(D)-Ala-Gly-MePhe-NH-NH-CO-CH$_2$-CH$_2$-O-CH$_2$-CH$_3$ is deprotected and purified to obtain 75 mg of the above-indicated compound. Rf$^2$=0.47; [α]$_D^{25}$+2.0°(c=0.2, MeOH); amino acid analysis: Gly, 1.00; Ala, 0.97; Tyr, 0.96; mean recovery rate 81%.

EXAMPLE 21

Production of
H-Tyr-(D)-Ala-Gly-MePhe-NH-NH-CO-CH$_2$-CH(CH$_3$)$_2$ (I) Production of
Z-Tyr-(D)-Ala-Gly-MePhe-NH-NH-CO-CH$_2$-CH(CH$_3$)$_2$ Using 426 mg of Z-Tyr-(D)-Ala-Gly-MePhe-NH-NH$_2$ and 0.09 ml of isovaleric acid, the procedure of Example 14-(I) is repeated to obtain 390 mg of the indicated compound (82%). m.p. 129°–133° C.; Rf$^1$=0.40; [α]$_D^{25}$−32.0 °(c=0.5, DMF)

Elemental analysis, for C$_{37}$H$_{46}$O$_8$N$_6$: Calcd.: C, 63.23; H, 6.60; N, 11.96; Found: C, 63.05; H, 6.45; N, 11.72.

(II) Production of
H-Tyr-(D)-Ala-Gly-MePhe-NH-NH-CO-CH$_2$-CH(CH$_3$)$_2$

In the same manner as Example 14-(II), 300 mg of Z-Tyr-(D)-Ala-Gly-MePhe-NH-NH-CO-CH$_2$-CH(CH$_3$)$_2$ is deprotected and purified to obtain 170 mg of the indicated compound. Rf$^2$=0.48; [α]$_D^{25}$−7.1° (c=0.2, MeOH), amino acid analysis: Gly, 1.00; Ala, 1.05; Tyr, 0.89; mean recovery rate 79%.

EXAMPLE 22

Production of
H-Tyr-(D)-Ala-Gly-MePhe-NH-NH-CO-CH$_2$-CH$_2$-Cl (I) Production of
Z-Tyr-(D)-Ala-Gly-MePhe-NH-NH-CO-CH$_2$-CH$_2$-Cl Using 482 mg of Z-Tyr-(D)-Ala-Gly-MePhe-NH-NH$_2$ and 0.12 g of 3-chloropropionic acid, the procedure of Example 14-(1) is repeated to obtain 420 mg of the indicated compound (85%). m.p. 126°–129° C.; Rf$^1$=0.38; [α]$_D^{25}$−28.6° (c=0.5, DMF)

Elemental analysis, for C$_{35}$H$_{41}$O$_8$N$_6$·Cl: Calcd.: C, 59.27; H, 5.82; N, 11.85; Cl, 5.00; Found: C, 59.33; H, 5.94; N, 11.61; Cl, 4.88.

(II) Production of
H-Tyr-(D)-Ala-Gly-MePhe-NH-NH-CO-CH$_2$-CH$_2$-Cl

In the same manner as Example 14-(II), 250 mg of Z-Tyr-(D)-Ala-Gly-MePhe-NH-NH-CO-CH$_2$-CH$_2$-Cl is deprotected and purified to obtain 105 mg of the indicated compound. Rf$^2$=0.50; [α]$_D^{25}$−6.9° (c=0.2, MeOH); amino acid analysis: Gly, 1.00; Ala, 0.96; Tyr, 0.92; mean recovery rate 81%.

EXAMPLE 23

Production of
H-Tyr-(D)-Ala-Gly-MePhe-NH-NH-CO-CH(OH)-CH$_3$ (I) Production of
Z-Tyr-(D)-Ala-Gly-MePhe-NH-NH-CO-CH(OH)-CH$_3$ Using 426 mg of Z-Tyr-(D)-Ala-Gly-MePhe-NH-NH$_2$ and 0.08 ml of lactic acid, the procedure of Example 14-(I) is repeated to obtain 380 mg of the indicated compound (81%). m.p. 131°–134° C.; Rf$^1$=0.29; $[\alpha]_D^{25}$ −29.6° (c=0.4, DMF)

Elemental analysis, for C$_{35}$H$_{42}$O$_9$N$_6$: Calcd.: C, 60.85; H, 6.12; N, 12.16; Found: C, 60.77; H, 5.96; N, 12.03.

(II) Production of
H-Tyr-(D)-Ala-Gly-MePhe-NH-NH-CO-CH(OH)-CH$_3$

In the same manner as Example 14-(II), 300 mg of Z-Tyr-(D)-Ala-Gly-MePhe-NH-NH-CO-CH(OH)-CH$_3$ is deprotected and purified to obtain 160 mg of the indicated compound. Rf$^2$=0.41; $[\alpha]_D^{25}$ −7.1° (c=0.2 MeOH); amino acid analysis; Gly, 1.00, Ala, 0.98; Tyr, 0.91; mean recovery rate 82%.

EXAMPLE 24

Production of
H-Tyr-(D)-Ala-Gly-MePhe-NH-NH-CO-O-CH$_2$-CH$_3$ (I) Production of
Z-Tyr-(D)-Ala-Gly-MePhe-NH-NH-CO-O-CH$_2$-CH$_3$ In 5 ml of DMF is dissolved 426 mg of Z-Tyr-(D)-Ala-Gly-MePhe-NH-NH$_2$, and after cooling, 90 mg of ethyl chlorocarbonate and 0.11 ml of TEA are added. The mixture is stirred at 0° C. for 2 hours. To the reaction mixture is added an aqueous solution of sodium chloride and the mixture is extracted with 100 ml of AcOEt and washed with water. The AcOEt layer is dried over anhydrous sodium sulfate and distilled under reduced pressure, the residue being then treated with diethyl ether, collected by filtration and reprecipitated from ethanol-diethyl ether. 350 mg (73%); m.p. 131°–133° C.; Rf$^1$=0.40; $[\alpha]_D^{25}$ −32.2° (c=0.3, DMF)

Elemental analysis, for C$_{35}$H$_{42}$O$_9$N$_6$: Calcd.: C, 60.85; H, 6.13; N, 12.16; Found: C, 60.67; H, 6.30; N, 12.11.

(II) Production of
H-Tyr-(D)-Ala-Gly-MePhe-NH-NH-CO-O-CH$_2$-CH$_3$

In the same manner as Example 14-(II), 250 mg of Z-Tyr-(D)-Ala-Gly-MePhe-NH-NH-CO-O-CH$_2$-CH$_3$ is deprotected and purified to obtain 105 mg of the indicated compound. Rf$^2$=0.47; $[\alpha]_D^{25}$ −6.7° (c=0.2, MeOH); amino acid analysis: Gly, 1.00; Ala, 0.99; Tyr, 0.88; mean recovery rate 79%.

EXAMPLE 25

Production of
H-Tyr-(D)-Ala-Gly-MePhe-NH-NH-CO-CH$_2$-CH$_2$-CH$_2$-CH$_3$ (I) Production of
Z-Tyr-(D)-Ala-Gly-MePhe-NH-NH-CO-CH$_2$-CH$_2$-CH$_2$-CH$_3$ Using 426 mg of Z-Tyr-(D)-Ala-Gly-MePhe-NH-NH$_2$ and 0.09 ml of n-valeric acid, the procedure of Example 14-(I) is repeated to obtain the indicated compound. 390 mg (82%); m.p. 131°–133° C.; Rf$^1$=0.40; $[\alpha]_D^{25}$ −31.4° (c=0.3, DMF)

Elemental analysis, for C$_{37}$H$_{46}$O$_8$N$_6$: Calcd.: C, 63.23; H, 6.60; N, 11.96; Found: C, 63.42; H, 6.71; N, 11.72.

(II) Production of
H-Tyr-(D)-Ala-Gly-MePhe-NH-NH-CO-CH$_2$-CH$_2$-CH$_2$-CH$_3$

In the same manner as Example 14-(II), 300 mg of Z-Tyr-(D)-Ala-Gly-MePhe-NH-NH-CO-CH$_2$-CH$_2$-CH$_2$-CH$_3$ is deprotected and purified to obtain 150 mg of the indicated compound. Rf$^2$=0.49; $[\alpha]_D^{25}$ −6.4° (c=0.2, MeOH); amino acid analysis: Gly, 1.00; Ala, 1.00; Tyr, 0.94; mean recovery rate 80%.

EXAMPLE 26

Production of
H-Tyr-(D)-Met(O)-Gly-Phe-NH-NH-CO-CH$_2$-CH$_3$ (I) Production of Z-Phe-NH-NH$_2$:

In 200 ml of MeOH is dissolved 59 g of Z-Phe-OH, followed by adding 5 ml of 6 N hydrochloric acid-dioxane, and the mixture is allowed to stand overnight at room temperature. The MeOH is distilled off, and the residue is dissolved in 300 ml of diethyl ether, followed by washing with water. After drying over anhydrous sodium sulphate, the diethyl ether is distilled off, and the residue is dissolved in 150 ml of MeOH.

16 ml of hydrazine hydrate is added to the solution, which is then allowed to stand at room temperature for 2 days. The MeOH is distilled off, and the precipitated crystals are collected by filtration with petroleum ether, washed well with diethyl ether, and recrystallized from AcOEt-petroleum ether. Thus obtained is 49 g (79%) of the desired product, m.p. 159°–160° C., Rf$^1$=0.62, $[\alpha]_D^{21}$ −9.8° (c=0.8, DMF)

Elemental analysis, for C$_{17}$H$_{19}$O$_3$N$_3$: Calculated: C, 65.16; H, 6.11; N, 13.41; Found: C, 65.02; H, 6.32; N, 13.20.

(II) Production of Z-Phe-NH-NH-CO-CH$_2$-CH$_3$

In 30 ml of DMF is dissolved 12.5 g of Z-Phe-NH-NH$_2$, followed by the addition of 5.8 ml of anhydrous propionic acid and 3 ml of pyridine after cooling, and the mixture is stirred overnight at room temperature. Water is added to the reaction solution, and the precipitate is collected by filtration. Recrystallization from MeOH-acetonitrile yields 9.8 g (68%) of the desired product, m.p. 203°–204° C., Rf$^1$=0.60, $[\alpha]_D^{21}$ −17.6° (c=0.46, DMF).

Elemental analysis, for C$_{20}$H$_{23}$O$_4$N$_3$: Calculated: C, 65.92; H, 6.27; N, 10.25; Found: C, 65.87; H, 6.72; N, 9.93.

(III) Production of Z-Gly-Phe-NH-NH-CO-CH$_2$-CH$_3$:

In 50 ml of MeOH is dissolved 2.2 g of Z-Phe-NH-NH-CO-CH$_2$-CH$_3$ to conduct a catalytic reduction with palladium black used as the catalyst. Following the removal of the catalyst by filtration, the MeOH is distilled off and the residue is dissolved in 10 ml of DMF. 2.2 g of Z-Gly-ONB is added to the solution, which is stirred overnight at room temperature. The DMF is distilled off, and the residue is extracted with 100 ml of AcOEt, followed by washing with water and drying over anhydrous sodium sulphate. The AcOEt is distilled off and the precipitated crystals are collected by filtration and recrystallized from AcOEt-acetonitrile.

Thus obtained is 1.8 g (71%) of the desired product, m.p. 151°–152° C., $Rf^1=0.46$, $[\alpha]_D^{21} -1.2°$ (c=0.5, DMF)

Elemental analysis, for $C_{22}H_{26}O_5N_4$: Calculated: C, 61.96; H, 6.15; N, 13.14; Found: C, 62.25; H, 6.23; N, 12.85.

(IV) Production of BOC-(D)-Met(O)-Gly-Phe-NH-NH-CO-$CH_2$-$CH_3$

In 50 ml of MeOH is dissolved 1.0 g of Z-Gly-Phe-NH-NH-CO-$CH_2$-$CH_3$ to conduct catalytic reduction with palladium black used as the catalyst. Following the removal of the catalyst by filtration, the MeOH is distilled off and the residue is dissolved in 20 ml of acetonitrile.

BOC-D-Met-ONB (prepared by the DCC method from 600 mg of BOC-D-Met-OH and 470 mg of HONB) is added to the solution, which is stirred overnight at room temperature.

0.5 ml of a 30% aqueous hydrogen peroxide solution is added to the reaction solution, followed by stirring at room temperature for 10 hours. The excess of hydrogen peroxide is decomposed wih palladium black, and the acetonitrile is distilled off. The resultant residue is extracted with 100 ml of n-butanol, and the extract is washed with water. The n-butanol is distilled off and the residue is treated with diethyl ether. Thus obtained is 1.1 g (88%) of the desired product, m.p. 121°–122° C., $Rf^1=0.40$, $[\alpha]_D^{21}$ 0° (c=0.5, DMF)

Elemental analysis, for $C_{24}H_{37}O_6N_5S \cdot \frac{1}{2}H_2O$: Calculated: C, 52.53; H, 6.97; N, 12.76; S, 5.84; Found: C, 52.41; H, 6.99; N, 12.46; S, 5.61.

(V) Production of BOC-Tyr-(D)-Met(O)-Gly-Phe-NH-NH-CO-$CH_2$-$CH_3$

In 10 ml of TFA is dissolved 0.82 g of BOC-(D)-Met-(O)-Gly-Phe-NH-NH-CO-$CH_2$-$CH_3$, and the mixture is allowed to stand at room temperature for 20 minutes. The TFA is distilled off and the residue is treated with diethyl ether, followed by recovering by filtration. The resultant powder is dissolved in 10 ml of DMF and, followed by the addition of 710 mg of BOC-Tyr-ONB and 0.3 ml of TEA, the mixture is stirred overnight at room temperature. The DMF is distilled off, and the residue is extracted with 100 ml of n-butanol, which is washed with water. The n-butanol is distilled off, and the residue is treated with diethyl ether. Thus obtained is 0.75 g (72%) of the desired product as crystals, m.p. 134°–135° C., $Rf^1=0.20$, $[\alpha]_D^{21}$ 0° (c=0.5, DMF)

Elemental analysis, for $C_{33}H_{46}O_9N_6S \cdot H_2O$: Calculated: C, 54.98; H, 6.71; N, 11.66; S, 4.44; Found: C, 54.72; H, 6.82; N, 11.16; S, 4.43.

(VI) Production of H-Tyr-(D)-Met(O)-Gly-Phe-NH-NH-CO-$CH_2$-$CH_3$

In 4 ml of TFA is dissolved 400 mg of BOC-Tyr-(D)-Met(O)-Gly-Phe-NH-NH-CO-$CH_2$-$CH_3$, and the mixture is allowed to stand at room temperature for 20 minutes. The TFA is distilled off, and the residue is treated with diethyl ether, followed by collecting by filtration. The resultant powder is dissolved in 30 ml of water, and the solution is allowed to pass through a column packed with Amberlite IRA-410 (acetic acid type, 2×6 cm), then the effluent and the washing are combined and subjected to freeze-drying. The resulting powder is dissolved in a small amount of 0.1 N aqueous acetic acid solution, and the solution is passed through a column packed with Sephadex LH-20, followed by eluting with 0.1 N aqueous acetic acid solution. The elution fractions from 310 ml to 330 ml are collected and freeze-dried. Thus obtained is 310 mg of the desired product, $Rf^2=0.35$, $[\alpha]_D^{21}+24.3°$ (c=0.35, MeOH), amino acid analysis (hydrochloric acid hydrolyzate): Gly 1.00, Met 0.57, Tyr 0.88, Phe 1.00.

EXAMPLE 27

Production of H-Tyr-(D)-Met(O)-Gly-Phe-NH-NH-CO-$CH_2$-$CH_2$-$CH_3$

(I) Production of Z-Tyr-(D)-Met(O)-Gly-Phe-OEt

In 50 ml of acetonitrile is dissolved 4.8 g of H-Phe-OEt·hydrochloride. After cooling, 2.8 ml of TEA and 7.4 g of Z-Gly-ONB are added, and the mixture is stirred overnight at room temperature. The solvent is distilled off, and the residue is extracted with 200 ml of AcOEt, followed by washing with water and drying over anhydrous sodium sulphate. The AcOEt is distilled off, and the residue is dissolved in 100 ml of MeOH to conduct catalytic reduction with palladium black used as the catalyst. After removal of the catalyst by filtration, the MeOH is distilled off and the residue is dissolved in 50 ml of acetonitrile. BOC-(D)-Met-ONB (prepared by DCC method from 4.7 g of BOC-(D)-Met-OH and 3.7 g of HONB) is added to the solution, which is then stirred overnight at room temperature. One ml of N-aqueous hydrochloric acid solution and 2.2 ml of 30% aqueous hydrogen peroxide solution are added to the reaction solution to be stirred at room temperature for 10 hours. The excess of the hydrogen peroxide is decomposed with palladium black, and the acetonitrile is distilled off. The resultant residue is extracted with 200 ml of AcOEt, followed by washing with water and drying over anhydrous sodium sulphate. The AcOEt is distilled off, and the residue is dissolved in 30 ml of TFA. The solution is allowed to stand at room temperature for 20 minutes. The TFA is distilled off, and the residue is treated with diethyl ether and collected by filtration. The resultant powder is dissolved in 60 ml of acetonitrile, and after cooling, 2.5 ml of TEA and 7.2 g of Z-Tyr-ONB are added to the solution, which is stirred overnight at room temperature. The solvent is distilled off and the residue is extracted with 200 ml of AcOEt, followed by washing with water and drying over anhydrous sodium sulphate. The AcOEt is distilled off and the precipitated crystals are collected by filtration. Recrystallization from AcOEt yields 6.9 g of the desired product, m.p. 162°–163° C., $Rf^1=0.42$, $[\alpha]_D^{21}-3.2°$ (c=0.37, DMF).

Elemental analysis, for $C_{35}H_{42}O_9N_4S$: Calculated: C, 60.50; H, 6.09; N, 8.06; S, 4.61; Found: C, 60.45; H, 6.38; N, 8.07; S, 4.37.

(II) Production of Z-Tyr-(D)-Met(O)-Gly-Phe-NH-$NH_2$ 6.0 g of Z-Tyr-(D)-Met(O)-Gly-Phe-OEt is dissolved in a mixed solvent of 20 ml of ethyl alcohol-20 ml of DMF, and 2 ml of hydrazine hydrate is added to the solution, which is then allowed to stand at room temperature for 2 days. The ethyl alcohol is distilled off, followed by adding diethyl ether, and the precipitated crystals are collected by filtration. The crystals are boiled with acetonitrile for washing. The yield of the product is 5.0 g, m.p. 182°–184° C., $Rf^1=0.10$, $[\alpha]_D^{21}-13.4°$ (c=0.44, DMF), Elemental analysis; for $C_{33}H_{40}O_8N_6S$: Calculated: C, 58.21; H, 5.92; N, 12.34; S, 4.71; Found: C, 57.95; H, 5.98; N, 12.10; S, 4.55.

(III) Production of Z-Tyr-(D)-Met(O)-Gly-Phe-NH-NH-CO-CH$_2$-CH$_2$-CH$_3$

In 5 ml of DMF are dissolved 0.51 g of Z-Tyr-(D)-Met(O)-Gly-Phe-NHNH$_2$ and 0.08 ml of n-butyric acid. After cooling to 0° C., 120 mg of HOBT and 190 mg of DCC are added and the mixture is stirred at 0° C. for 5 hours and then at room temperature overnight. The DMF is distilled off, and the residue is treated with diethyl ether, followed by purifying by reprecipitation with MeOH-acetonitrile. Thus obtained is 410 mg of the desired product, m.p. 161°–163° C., Rf$^1$=0.31, $[\alpha]_D^{21}$ −8.8° (c=0.34, DMF)

Elemental analysis, for $C_{37}H_{46}O_9N_6S$: Calculated: C, 59.18; H, 6.17; N, 11.19; S, 4.27; Found: C, 58.85; H, 6.02; N, 10.86; S, 4.05.

(IV) Production of H-Tyr-(D)-Met(O)-Gly-Phe-NH-NH-CO-CH$_2$-CH$_2$-CH$_3$

In 3 ml of methane sulphonic acid in the presence of 0.3 ml of anisole is dissolved 300 ml of Z-Tyr-(D)-Met-(O)-Gly-Phe-NH-NH-CO-CH$_2$-CH$_2$-CH$_3$. After standing at room temperature for 30 minutes, diethyl ether is added to the reaction solution, which is then allowed to stand at −20° C. for 30 minutes. Following removal of the supernatant solution, the resultant oily substance is dissolved in 30 ml of water to pass through a column packed with Amberlite IRA-410 (acetic acid type, 2×6 cm). The effluent and the washings are combined and freeze-dried. The resulting powder is dissolved in a small amount of 0.1 N aqueous acetic acid solution to pass through a column packed with Sephadex LH-20 (2.5×125 cm), followed by eluting with 0.1 N aqueous acetic acid solution. The elution fractions from 275 ml to 290 ml are collected and freeze-dried. Thus obtained is 110 mg of the desired product, Rf$^2$=0.37, $[\alpha]_D^{21}$ +23.7° (c=0.32, MeOH), amino acid analysis (hydrochloric acid hydrolyzate): Gly 1.00, Met 0.38, Tyr, 0.91, Phe 1.05.

EXAMPLE 28

Production of H-Tyr-(D)-Met(O)-Gly-Phe-NH-NH-CO-CH(CH$_3$)$_2$ (I) Production of Z-Tyr-(D)-Met(O)-Gly-Phe-NH-NH-CO-CH(CH$_3$)$_2$ Using 0.51 g of Z-Tyr-(D)-Met(O)-Gly-Phe-NH-NH$_2$ and 0.08 ml of isobutyric acid, obtained in a similar manner to (III) of Example 27 is 440 mg of the desired product, m.p. 181°–183° C., $[\alpha]_D^{21}$ −8.3° (c=0.37, DMF), Rf$^1$=0.32, Elemental analysis, for $C_{37}H_{46}O_9N_6S$: Calculated: C, 59.18; H, 6.17; N, 11.19; S, 4.27; Found: C, 58.77; H, 6.01; N, 10.82; S, 4.15.

(II) Production of H-Tyr-(D)-Met(O)-Gly-Phe-NH-NH-CO-CH(CH$_3$)$_2$

Using 300 mg of Z-Tyr-(D)-Met(O)-Gly-Phe-NH-NH-CO-CH(CH$_3$)$_2$, obtained in a similar manner to (IV) of Example 27 is 105 mg of the desired product, Rf$^2$=0.37, $[\alpha]_D^{21}$ +26.8° (c=0.32, MeOH), amino acid analysis (hydrochloric acid hydrolyzate): Gly 1.00, Met 0.38, Tyr 0.89, Phe 1.02.

EXAMPLE 29

Production of H-Tyr-(D)-Met(O)-Gly-Phe-NH-NH-CO-CH$_3$ (I) Production of Z-Tyr-(D)-Met(O)-Gly-Phe-NH-NH-CO-CH$_3$ Using 0.51 g of Z-Tyr-(D)-Met(O)-Gly-Phe-NH-NH$_2$ and 0.06 ml of acetic acid, obtained in a similar manner to (III) of Example 27 is 405 mg of the desired product, m.p. 180°–182° C., Rf$^1$=0.28, $[\alpha]_D^{21}$ −9.1° (c=0.30, DMF)

Elemental analysis, for $C_{35}H_{42}O_9N_6S \cdot H_2O$: Calculated: C, 56.75; H, 5.72; N, 11.34; S, 4.33; Found: C, 56.48; H, 5.62; N, 11.08; S, 4.05.

(II) Production of H-Tyr-(D)-Met(O)-Gly-Phe-NH-NH-CO-CH$_3$

Using 300 mg of Z-Tyr-(D)-Met(O)-Gly-Phe-NH-NH-CO-CH$_3$, obtained in a similar manner to (IV) of Example 27 is 130 mg of the desired product, Rf$^2$=0.30, $[\alpha]_D^{21}$ +19.6° (c=0.27, MeOH), amino acid analysis (hydrochloric acid hydrolyzate): Gly 1.00, Met 0.35, Tyr 0.91, Phe 1.02.

EXAMPLE 30

Production of H-Tyr-(D)-Met(O)-Gly-Phe-NH-NH-CO-(CH$_2$)$_3$-CH$_3$ (I) Production of Z-Tyr-(D)-Met(O)-Gly-Phe-NH-NH-CO-(CH$_2$)$_3$-CH$_3$ Using 0.47 g of Z-Tyr-(D)-Met(O)-Gly-Phe-NH-NH$_2$ and 0.1 ml of n-valeric acid, obtained in a similar manner to (III) of Example 27 is 0.39 g of the desired product, m.p. 159°–161° C., Rf$^1$=0.33, $[\alpha]_D^{21}$ −8.6° (c=0.4, DMF)

Elemental analysis, for $C_{38}H_{48}O_9N_6S$: Calculated: C, 59.66; H, 6.32; N, 10.98; S, 4.19; Found: C, 59.39; H, 6.42; N, 10.69; S, 4.06.

(II) Production of H-Tyr-(D)-Met(O)-Gly-Phe-NH-NH-CO-(CH$_2$)$_3$-CH$_3$

Using 300 mg of Z-Tyr-(D)-Met(O)-Gly-Phe-NH-NH-CO-(CH$_2$)$_3$-CH$_3$, obtained in a similar manner to (IV) of Example 27 is 110 mg of the desired product, Rf$^2$=0.38, $[\alpha]_D^{21}$ +24.8° (c=0.32, MeOH), amino acid analysis (acid hydrolyzate): Gly 1.00, Met 0.29, Tyr 0.89, Phe 1.00.

EXAMPLE 31

Production of H-Tyr-(D)-Met(O)-Gly-Phe-NH-NH-CO-(CH$_2$)$_4$-CH$_3$ (I) Production of Z-Tyr-(D)-Met(O)-Gly-Phe-NH-NH-CO-(CH$_2$)$_4$-CH$_3$ 0.51 g of Z-Tyr-(D)-Met(O)-Gly-Phe-NH-NH$_2$ and 0.09 ml of n-caproic acid, obtained in a similar manner to (III) of Example 27 is 430 mg of the desired product, m.p. 170°–172° C., Rf$^1$=0.34, $[\alpha]_D^{21}$ −9.1° (c=0.48, DMF)

Elemental analysis, for $C_{39}H_{50}O_9N_6S$: Calculated: C, 60.13; H, 6.47; N, 10.79; S, 4.11; Found: C, 59.88; H, 6.42; N, 10.53; S, 4.22.

(II) Production of H-Tyr-(D)-Met(O)-Gly-Phe-NH-NH-CO-(CH₂)₄-CH₃

Using 350 mg of Z-Tyr-(D)-Met(O)-Gly-Phe-NH-NH-CO-(CH₂)₄-CH₃, obtained in a similar manner to (IV) of Example 27 is 210 mg of the desired product, $Rf^2=0.42$, $[\alpha]_D^{21}+25.7°$ (c=0.30, MeOH), amino acid analysis (hydrochloric acid hydrolyzate): Gly, 1.00, Met 0.29, Tyr 0.88, Phe 0.99.

EXAMPLE 32

Production of H-Tyr-(D)-Met(O)-Gly-Phe-NH-NH-CO-(CH₂)₂-O-CH₂-CH₃

(I) Production of Z-Tyr-(D)-Met(O)-Gly-Phe-NH-NH-CO-(CH₂)₂-O-CH₂-CH₃

Using 0.51 g of Z-Tyr-(D)-Met(O)-Gly-Phe-NH-NH₂ and 0.09 ml of β-ethoxypropionic acid, obtained in a similar manner to (III) of Example 27 is 440 mg of the desired product, m.p. 159°–161° C., $Rf^1=0.32$, $[\alpha]_D^{21}-7.5°$ (c=0.48, DMF)

Elemental analysis, for $C_{38}H_{48}O_{10}N_6S$: Calculated: C, 58.44; H, 6.19; N, 10.76; S, 4.10; Found: C, 58.22; H, 6.31; N, 10.59; S, 3.99.

(II) Production of H-Tyr-(D)-Met(O)-Gly-Phe-NH-NH-CO-(CH₂)₂-O-CH₂-CH₃

Using 350 mg of Z-Tyr-(D)-Met(O)-Gly-Phe-NH-NH-CO-(CH₂)₂-O-CH₂-CH₃, obtained in a similar manner to (IV) of Example 27 is 105 mg of the desired product, $Rf^2=0.40$, $[\alpha]_D^{21}+25.1°$ (c=0.37), amino acid analysis (acid hydrolyzate): Gly 1.00, Met 0.32, Tyr 0.89, Phe 0.98.

EXAMPLE 33

Production of H-Tyr-(D)-Met(O)-Gly-Phe-NH-NH-CO-O-CH₂-CH₃

(I) Production of BOC-(D)-Met-Gly-OEt

In 100 ml of THF are dissolved 10.0 g of BOC-(D)-Met-OH and 7.9 g of HONB, followed by cooling at 0° C. and adding 9.0 g of DCC, and the mixture is stirred at 0° C. for 6 hours. Insoluble matters are filtered out, and 5.9 g of H-Gly-OEt·HCl salt and 5.6 ml of TEA are added to the filtrate, which is then stirred overnight at room temperature. The THF is distilled off and the residue is extracted with 100 ml of AcOEt, followed by washing with water and drying over anhydrous sodium sulphate. The AcOEt is distilled off and the residue is crystallized with petroleum ether. Recrystallization from AcOEt-petroleum ether yields 9.8 g of the desired product, m.p. 55°–56° C., $Rf^1=0.70$, $[\alpha]_D^{21}+2.5°$ (c=0.67, DMF)

Elemental analysis, for $C_{14}H_{26}O_5N_2S$: Calculated: C, 50.28; H, 7.83; N, 8.37; S, 9.59; Found: C, 50.88; H, 7.99; L N, 8.46; L S, 9.42.

(II) Production of BOC-Tyr-(D)-Met-Gly-OEt

In 15 ml of TFA is dissolved 3.0 g of BOC-(D)-Met-Gly-OEt, and the mixture is allowed to stand at room temperature for 10 minutes. The TFA is distilled off and the residue is treated with diethyl ether, followed by recovering by filtration. The resultant powder is dissolved in 20 ml of THF. After cooling, 1.6 ml of TEA and 4.0 g of BOC-Tyr-ONB are added, and the mixture is stirred overnight at room temperature. The THF is distilled off, and the residue is extracted with 100 ml of AcOEt, followed by washing with water and drying over anhydrous sodium sulphate. The AcOEt is distilled off and the residue is crystallized with petroleum ether. Recrystallization from AcOEt yields 3.1 g of the desired product, m.p. 121°–122° C., $Rf^1=0.62$, $[\alpha]_D^{21}+16.8°$ (c=0.40, DMF)

Elemental analysis, for $C_{23}H_{35}O_7N_3S$: Calculated: C, 55.51; H, 7.09; N, 8.44; S, 6.44; Found: C, 55.32; H, 6.93; N, 8.25; L S, 6.27.

(III) Production of BOC-Tyr-(D)-Met-Gly-OH

In 30 ml of MeOH is dissolved 2.8 g of BOC-Tyr-(D)-Met-Gly-OEt. After cooling, 12 ml of N-aqueous sodium hydroxide solution is added, and the mixture is stirred at room temperature for 1 hour. After cooling, 60 ml of 0.2 N-aqueous hydrochloric acid solution is added, and the precipitated crystals are collected by filtration, followed by washing with cold water. Thus obtained is 2.3 g of the desired product, m.p. 184°–186° C., $Rf^1=0.24$, $[\alpha]_D^{21}+13.3°$ (c=0.46, DMF)

Elemental analysis, for $C_{21}H_{31}O_7N_3S$: Calculated: C, 53.71; H, 6.65; N, 8.94; S, 6.83; Found: C, 54.32; H, 6.71; N, 8.49; S, 6.70.

(IV) Production of BOC-Tyr-(D)-Met(O)-Gly-OH

In a mixed solvent comprising 10 ml of MeOH and 5 ml of acetic acid is dissolved 2.2 g of BOC-Tyr-(D)-Met-Gly-OH, followed by adding 0.6 ml of 30% aqueous hydrogen peroxide solution, and the mixture is stirred at room temperature for 5 hours. Following the addition of a small amount of palladium black, the mixture is stirred. The catalyst is filtered out, and the solvent is distilled off, whereby the precipitated crystals are collected by filtration. Thus obtained is 2.1 g of the desired product, m.p. 185° C. (decomposed), $Rf^1=0.20$, $[\alpha]_D^{21}+1.8°$ (c=0.5, DMF)

Elemental analysis, for $C_{21}H_{31}O_8N_3S\cdot H_2O$: Calculated: C, 50.08; H, 6.20; N, 8.35; S, 6.36; Found: C, 49.77; H, 6.32; N, 8.25; S, 6.10.

(V) Production of BOC-Tyr-(D)-Met(O)-Gly-Phe-NH-NH-CO-O-CH₂CH₃

In 50 ml of MeOH is dissolved 460 mg of Z-Phe-NH-NH-CO-O-CH₂-CH₃, and the catalytic reduction is conducted with palladium black used as the catalyst. After filtering the catalyst, the MeOH is distilled off, and the residue is dissolved in 10 ml of DMF. On the other hand, 485 mg of BOC-Tyr-(D)-Met(O)-Gly-OH and 215 mg of HONB are dissolved in 5 ml of DMF; after cooling to 0° C., 230 mg of DCC is added, and the mixture is stirred at 0° C. for 6 hours. Following filtration of the insoluble matters, the filtrate is combined with the amine component, and the mixture is stirred at room temperature overnight. The DMF is distilled off, and the residue is extracted with 50 ml of n-butanol, followed by washing with water. The n-butanol is distilled off, and the residue is treated with diethyl ether, followed by collecting by filtration. Thus obtained is 630 mg of the desired product, m.p. 145°–147° C., $Rf^1=0.28$, $[\alpha]_D^{21}-3.6°$ (c=0.5, DMF)

Elemental analysis, for $C_{33}H_{46}O_{10}N_6S$: Calculated: C, 55.13; H, 6.45; N, 11.69; S, 4.46; Found: C, 54.85; H, 6.29; N, 11.45; S, 4.35.

(VI) Production of
H-Tyr-(D)-Met(O)-Gly-Phe-NHNH-CO-O-CH$_2$-CH$_3$

Using 350 mg of BOC-Tyr-(D)-Met(O)-Gly-Phe-NH-NH-CO-O-CH$_2$-CH$_3$, obtained in a similar manner to (VI) of Example 26 is the desired product; yield: 205 mg, Rf$^2$=0.39, $[\alpha]_D^{21}$+15.0° (c=0.38, MeOH), amino acid analysis (acid hydrolyzate); Gly 1.00, Met 0.22, Tyr 0.88, Phe 1.00.

EXAMPLE 34
Production of
H-Tyr-(D)-Met(O)-Gly-Phe-NH-NH-CO-CH$_2$-S-CH$_3$ (I) Production of BOC-Phe-NH-NH-CO-CH$_2$-S-CH$_3$ In 20 ml of acetonitrile is dissolved 1.4 ml of ethyl thioglycolate, and 1 ml of methyl iodide is added. While the mixture is stirred under cooling, 2.1 ml of TEA is added dropwise, and the mixture is stirred at room temperature for 3 hours. The acetonitrile is distilled off, and the residue is extracted with diethyl ether, followed by washing with water and drying over anhydrous sodium sulphate. The diethyl ether is distilled off, and the residue is dissolved in MeOH, followed by adding 0.7 ml of hydrazine hydrate and allowing to stand at room temperature for 2 days. The MeOH is distilled off and the residue is dissolved in 20 ml of DMF. To the solution is added 3.2 g of BOC-Phe-ONB, and the mixture is stirred overnight at room temperature. The DMF is distilled off, and the residue is extracted with 100 ml of AcOEt, followed by washing with water and drying over anhydrous sodium sulphate. The AcOEt is distilled off, and the precipitated crystals are collected by filtration. Recrystallization from AcOEt-petroleum ether yields 2.3 g of the desired product, m.p. 151°–152° C., Rf$^1$=0.66, $[\alpha]_D^{21}$−18.6° (c=0.5, DMF)

Elemental analysis, for C$_{17}$H$_{25}$O$_4$N$_3$S; Calculated: C, 55.55; H, 6.86; N, 11.44; S, 8.73; Found: C, 55.59; H, 6.89; N, 11.23; S, 8.33.

(II) Production of
BOC-Tyr-(D)-Met(O)-Gly-Phe-NH-NH-CO-CH$_2$-S-CH$_3$

In 4 ml of TFA is dissolved 420 mg of BOC-Phe-NH-NH-CO-CH$_2$-S-CH$_3$, and the mixture is allowed to stand at room temperature for 20 minutes. The TFA is distilled off and the residue is treated with diethyl ether, followed by collecting by filtration. The resultant powder is dissolved in 10 ml of DMF, and to the solution is added 0.16 ml of TEA. On the other hand, in 5 ml of DMF is dissolved 485 mg of BOC-Tyr-D-Met(O)-Gly-OH and 215 mg of HONB, to which, after cooling to 0° C., 230 mg of DCC is added, and the mixture is stirred at 0° C. for 6 hours. After filtering the insoluble matters, the filtrate is combined with the previously prepared amine component, and the mixture is stirred overnight at room temperature. The DMF is distilled off, and the residue is treated with diethyl ether. Thus obtained is 630 mg of the desired product, m.p. 154°–156° C., Rf$^1$=0.25, $[\alpha]_D^{21}$−2.0° (c=0.46, DMF)

Elemental analysis, for C$_{33}$H$_{46}$O$_9$N$_6$S$_2$: Calculated: C, 53.93; H, 6.31; N, 11.43; S, 8.72; Found: C, 53.64; H, 6.42; N, 11.25; S, 8.45.

(III) Production of
H-Tyr-(D)-Met(O)-Gly-Phe-NH-NH-CO-CH$_2$-S-CH$_3$

Using 300 mg of BOC-Tyr-(D)-Met(O)-Gly-Phe-NH-NH-CO-CH$_2$-S-CH$_3$, obtained in a similar manner to (VI) of Example 26 is 220 mg of the desired product, Rf$^2$=0.42, $[\alpha]_D^{21}$+15.4° (c=0.33, MeOH), amino acid analysis (acid hydrolyzate): Gly 1.00, Met 0.38, Tyr 0.58, Phe 1.02.

EXAMPLE 35
Production of
H-Tyr-(D)-Met(O)-Gly-Phe-NH-NH-CO-CH$_2$-SO-CH$_3$

In 3 ml of N-aqueous acetic acid solution is dissolved 100 mg of H-Tyr-(D)-Met(O)-Gly-Phe-NH-NH-CO-CH$_2$-S-CH$_3$. While the solution is stirred, 0.1 ml of 30% aqueous hydrogen peroxide solution is added, and the mixture is stirred at room temperature for 5 hours. The powder produced by freeze-drying of the reaction solution is dissolved in a small quantity of 0.1 N-aqueous acetic acid solution, and the solution is applied to a column of Sephadex LH-20 (2.5×120 cm), followed by eluting with 0.1 N aqueous acetic acid solution. The elution fractions from 290 ml to 305 ml are collected and freeze-dried. Thus obtained is 70 mg of the desired product, Rf$^2$=0.32, $[\alpha]_D^{21}$+13.5° (c=0.46, MeOH), amino acid analysis (acid hydrolyzate): Gly 1.00, Met 0.29, Tyr 0.65, Phe 1.02.

EXAMPLE 36
Production of
H-Tyr-(D)-Met(O)-Gly-MePhe-NH-NH-CO-CH$_2$-CH$_3$ (I) Production of BOC-(D)-Met-Gly-OH In 20 ml of ethyl alcohol is dissolved 4.7 g of BOC-(D)-Met-Gly-OEt. After cooling, 16 ml of N-aqueous sodium hydroxide solution is added, and the mixture is stirred at room temperature for 1 hour. The ethyl alcohol is distilled off, and the residue, after adding aqueous citric acid solution to neutralize, is extracted with 100 ml of ethyl acetate, followed by washing with water and drying over anhydrous sodium sulphate. The AcOEt is distilled off and the residue is crystallized with petroleum ether. Recrystallization from AcOEt-petroleum ether results in a yield of 3.8 g of the desired product, m.p. 124°–125° C., Rf$^1$=0.41, $[\alpha]_D^{21}$+12.3° (c=0.59, DMF)

Elemental analysis, for C$_{12}$H$_{22}$O$_5$N$_2$S: Calculated: C, 47.04; H, 7.23; N, 9.14; S, 10.46; Found: C, 46.79; H, 7.45; N, 9.20; S, 10.21.

(II) Production of
BOC-(D)-Met(O)-Gly-MePhe-NH-NH-CO-CH$_2$-CH$_3$

In 50 ml of MeOH is dissolved 4.7 g of Z-MePhe-OH and 2 ml of 6 N-hydrochloric acid-dioxane is added, followed by allowing to stand overnight at room temperature. The MeOH is distilled off, and the residue, after washing with water, is extracted with 100 ml of AcOEt, followed by washing with water and drying over anhydrous sodium sulphate. The AcOEt is distilled off, and the residue is dissolved in 50 ml of MeOH, followed by adding 1.5 ml of hydrazine hydrate and allowing to stand at room temperature for 3 days. The MeOH is distilled off, and the residue is extracted with 100 ml of AcOEt, followed by washing with water and drying over anhydrous sodium sulphate. The AcOEt is distilled off, and the residue is dissolved in 20 ml of THF, followed by adding 1.4 ml of propionic anhydride. After cooling, 1.4 ml of TEA is added, and the mixture is stirred at room temperature for 5 hours. The THF is distilled off, and the residue is extracted with 100 ml of AcOEt, followed by washing with 5% aqueous sodium bicarbonate solution and drying over anhydrous sodium sulphate. The AcOEt is distilled off, resulting in 3.8 g of the oily product of Z-MePhe-NH-NH-CO-CH$_2$-CH$_3$, out of which 2.3 g is dissolved in 50 ml of MeOH to conduct catalytic reduction with palladium black used as catalyst. The catalyst is filtered out, and the MeOH is distilled off, whereby the resultant residue is dissolved in 10 ml of DMF.

On the other hand, in 20 ml of acetonitrile are dissolved 1.85 g of BOC-(D)-Met-Gly-OH and 1.2 g of HONB. After cooling at 0° C., 1.4 g of DCC is added, and the mixture is stirred at 0° C. for 4 hours. After filtrating out the insoluble matters, the filtrate is combined with the amine component, and the mixture is stirred overnight at room temperature. The solvent was distilled off, and the residue is dissolved in 100 ml of AcOEt and washed with water. The AcOEt solution is concentrated to 20 ml, to which 5 ml of acetic acid and 0.5 ml of 30% aqueous hydrogen peroxide solution are added, followed by stirring at room temperature for 5 hours. The reaction solution is extracted with 50 ml of n-butanol, and washed with water. The n-butanol is distilled off, and the residue is treated with diethyl ether, followed by collecting by filtration. Thus obtained is 1.9 g of the desired product, m.p. 116°–117° C., Rf$^1$=0.20, $[\alpha]_D^{21}$−25.7° (c=0.38, DMF)

Elemental analysis, for C$_{25}$H$_{39}$O$_7$N$_5$S: Calculated: C, 54.22; H, 7.09; N, 12.65; S, 5.79; Found: C, 54.05; H, 6.98; N, 12.41; S, 5.48.

(III) Production of
BOC-Tyr-(D)-Met(O)-Gly-MePhe-NH-NH-CO-CH$_2$-CH$_3$

In 4 ml of TFA is dissolved 420 mg of BOC-(D)-Met-(O)-Gly-MePhe-NH-NH-CO-CH$_2$-CH$_3$, and the mixture is allowed to stand at room temperature for 20 minutes. The TFA is distilled off, and the residue is treated with diethyl ether, followed by collecting by filtration and drying. The resultant powder is dissolved in 10 ml of DMF and, after cooling, 0.14 ml of TEA is added. The mixture, after adding 330 mg of BOC-Tyr-ONB, is stirred overnight at room temperature. The DMF is distilled off, and the residue is extracted with 50 ml of n-butanol, followed by washing with water. The n-butanol is distilled off, and the residue is treated with diethyl ether to be collected by filtration. Reprecipitation from methanol-diethyl ether yields 310 mg of the desired product, m.p. 138°–139° C., Rf$^1$=0.20, $[\alpha]_D^{21}$−21.3° (c=0.55, DMF)

Elemental analysis, for C$_{34}$H$_{48}$O$_9$N$_6$S: Calculated: C, 56.96; H, 6.74; N, 11.72; S, 4.47; Found: C, 56.58; H, 6.48; N, 11.58; S, 4.23.

(IV) Production of
H-Tyr-(D)-Met(O)-Gly-MePhe-NH-NH-CO-CH$_2$-CH$_3$

In 2 ml of TFA is dissolved 150 mg of BOC-Tyr-(D)-Met(O)-Gly-MePhe-NH-NH-CO-CH$_2$-CH$_3$, and the mixture is allowed to stand at room temperature for 30 minutes. The TFA is distilled off, and the residue is treated with diethyl ether, followed by collecting by filtration. The resultant powder is dissolved in a small amount of water, and the solution is passed through a column (2×4 cm) of Amberlite IRA-410 (acetic acid type), whereby the effluent and washing are combined to be freeze-dried. The obtained powder is purified in a similar manner to (VI) of Example 26 and, obtained is 60 mg of the desired product, Rf$^2$=0.33, $[\alpha]_D^{21}$+4.1° (c=0.21, MeOH), amino acid analysis (acid hydrolyzate): Gly 1.00, Met 0.24, Tyr 0.91.

EXAMPLE 37

Production of
H-MeTyr-(D)-Met(O)-Gly-Phe-NH-NH-CO-CH$_2$-CH$_3$ (I) Production of
Z-MeTyr(Bu$^t$)-(D)-Met(O)-Gly-Phe-NH-NH-CO-CH$_2$-CH$_3$ In 4 ml of TFA is dissolved 470 mg of BOC-(D)-Met-(O)-Gly-Phe-NH-NH-CO-CH$_2$-CH$_3$, and the mixture is allowed to stand at room temperature for 10 minutes. The TFA is distilled off, and the residue is treated with diethyl ether, followed by recovering by filtration. The resultant powder is dissolved in 10 ml of DMF. After cooling, 0.15 ml of TEA and Z-MeTyr(Bu$^t$)-ONB (prepared by DCC method from 380 mg of Z-MeTyr(Bu$^t$)-OH and 215 mg of HONB), and the mixture is stirred overnight at room temperature. The DMF is distilled off, and the residue is extracted with 100 ml of AcOEt, followed by washing with water and drying over anhydrous sodium sulphate. The AcOEt is distilled off, and the residue is treated with diethyl ether for collecting by filtration. Thus obtained is 450 mg of the desired product, Rf$^1$=0.46, $[\alpha]_D^{21}$−30.0° (c=0.5, DMF)

Elemental analysis, for C$_{39}$H$_{51}$O$_8$N$_5$S: Calculated: C, 62.46; H, 6.85; N, 9.34; S, 4.27; Found: C, 62.15; H, 6.63; N, 9.05; S, 3.91.

(II) Production of
H-MeTyr-(D)-Met(O)-Gly-Phe-NH-NH-CO-CH$_2$-CH$_3$

Using 350 mg of Z-MeTyr(Bu$^t$)-(D)-Met(O)-Gly-Phe-NH-NH-CO-CH$_2$-CH$_3$, obtained in a similar manner to (IV) of Example 27 is 120 mg of the desired product, Rf$^2$=0.34, $[\alpha]_D^{21}$+19.5° (c=0.20, MeOH), amino acid analysis (acid hydrolyzate): Gly 1.00, Met 0.32, Phe 0.98.

EXAMPLE 38

Production of
H-MeTyr-(D)-Met(O)-Gly-MePhe-NH-NH-CO-CH$_2$-CH$_3$ (I) Production of
Z-MeTyr(Bu$^t$)-(D)-Met(O)-Gly-MePhe-NH-NH-CO-CH$_2$-CH$_3$ In 4 ml of TFA is dissolved 550 mg of BOC-(D)-Met-(O)-Gly-MePhe-NH-NH-CO-CH$_2$-CH$_3$, and the mixture is allowed to stand at room temperature for 10 minutes. The TFA is distilled off, and the residue is treated with diethyl ether, followed by collecting by filtration and drying. The resultant powder is dissolved in 10 ml of DMF and, after cooling, 0.16 ml of TFA is added. Following the addition of Z-MeTyr(Bu$^t$)-ONB (prepared by DCC method from 385 mg of Z-MeTyr(-Bu$^t$)-OH and 210 mg of HONB), the mixture is stirred overnight at room temperature. The DMF is distilled off, and the residue is extracted with 100 ml of AcOEt, followed by washing with water and drying over anhydrous sodium sulphate. The AcOEt is distilled off, and the residue is treated with diethyl ether to be collected by filtration. Thus obtained is 450 mg of the desired product, m.p. 121°–123° C., Rf$^1$=0.48

Elemental analysis, for C$_{42}$H$_{56}$O$_9$N$_6$S·H$_2$O: Calculated: C, 60.12; H, 6.97; N, 10.01; S, 3.82; Found: C, 59.88; H, 6.86; N, 9.75; S, 3.91.

(II) Production of H-MeTyr-(D)-Met(O)-Gly-MePhe-NH-NH-CO-CH₂-CH₃

Using 250 mg of Z-MeTyr(Buᵗ)-(D)-Met(O)-Gly-MePhe-NH-NH-CO-CH₂-CH₃, obtained in a similar manner to (IV) of Example 27 is 105 mg of the desired product, $Rf^2=0.36$, amino acid analysis (hydrochloric acid hydrolyzate): Gly 1.00, Met 0.31.

EXAMPLE 39

Production of H-Tyr-(D)-Met(O)-Gly-Phe-NH-NH-CO-CH₂-CH₃-Cl (I) Production of Z-Tyr-(D)-Met(O)-Gly-Phe-NH-NH-CO-CH₂-CH₂-Cl Using 510 mg of Z-Tyr-(D)-Met(O)-Gly-Phe-NH-NH₂ and 100 mg of β-chloropropionic acid, obtained in a similar manner to (III) of Example 27 is 410 mg of the desired product, m.p. 172°–175° C., $Rf^1=0.26$, $[\alpha]_D^{21}-8.9°$ (c=0.50, DMF)

Elemental analysis, for $C_{36}H_{43}O_9N_6SCl\cdot H_2O$: Calculated: C, 54.78; H, 5.74; N, 10.65; S, 4.06; Cl, 4.49; Found: C, 54.45; H, 5.62; N, 10.54; S, 4.12; Cl, 4.03.

(II) Production of H-Tyr-(D)-Met(O)-Gly-Phe-NH-NH-CO-CH₂-CH₂-Cl:

Using 300 mg of Z-Tyr-(D)-Met(O)-Gly-Phe-NH-NH-CO-CH₂-CH₂-Cl, obtained in a similar manner to (IV) of Example 27 is 120 mg of the desired product, $Rf^2=0.37$, $[\alpha]_D^{21}+25.4°$ (c=0.40, MeOH), amino acid analysis (acid hydrolyzate): Gly 1.00, Met 0.40, Tyr 0.92, Phe 0.98.

EXAMPLE 40

Production of H-Tyr-(D)-Met(O)-Gly-Phe-NH-NH-CO-CH₂-CH₂-CO-CH₃

(I) Production of Z-Tyr-(D)-Met(O)-Gly-Phe-NH-NH-CO-CH₂-CH₂-CO-CH₃

Using 510 mg of Z-Tyr-(D)-Met(O)-Gly-Phe-NH-NH₂ and 110 mg of levulinic acid, obtained in a similar manner to (III) of Example 27 is 380 mg of the desired product, m.p. 161°–162° C., $Rf^1=0.25$, $[\alpha]_D^{21}-7.6°$ (c=0.35, DMF)

Elemental analysis, for $C_{38}H_{46}O_{10}N_6S\cdot H_2O$: Calculated: C, 57.27; H, 6.07; N, 10.54; S, 4.02; Found: C, 57.05; H, 6.12; N, 10.23; S, 3.85.

(II) Production of H-Tyr-(D)-Met(O)-Gly-Phe-NH-NH-CO-CH₂-CH₂-CO-CH₃

Using 350 mg of Z-Tyr-(D)-Met(O)-Gly-Phe-NH-NH-CO-CH₂-CH₂-CO-CH₃, obtained in a similar manner to (IV) of Example 27 is 130 mg of the desired product, $Rf^2=0.35$, $[\alpha]_D^{21}+26.0°$ (c=0.25, MeOH), amino acid analysis (acid hydrolyzate): Gly 1.00, Met 0.33, Tyr 0.98, Phe 1.02.

EXAMPLE 41

Production of H-Tyr-(D)-Met(O)-Gly-Phe-NH-NH-CO-CH₂-CH₂-OH (I) Production of BOC-Tyr-(D)-Met(O)-Gly-Phe-NH-NH-CO-CH₂-CH₂-OH Using 460 mg of Z-Phe-NH-NH-CO-CH₂-CH₂-OH and 485 mg of BOC-Tyr-(D)-Met(O)-Gly-OH, obtained in a similar manner to (V) of Example 33 is 620 mg of the desired product, m.p. 148°–150° C., $Rf^1=0.20$, $[\alpha]_D^{21}-2.6°$ (c=0.40, DMF)

Elemental analysis, for $C_{35}H_{46}O_{10}N_6S$: Calculated: C, 55.13; H, 6.45; N, 11.69; S, 4.46; Found: C, 54.86; H, 6.25; N, 11.42; S, 4.19.

(II) Production of H-Tyr-(D)-Met(O)-Gly-Phe-NH-NH-CO-CH₂-CH₂-OH:

By treating 350 mg of BOC-Tyr-(D)-Met(O)-Gly-Phe-NH-NH-CO-CH₂-CH₂-OH in a similar manner to (VI) of Example 26 is obtained 150 mg of the desired product, $Rf^2=0.30$, $[\alpha]_D^{21}+19.4°$ (c=0.35, MeOH), amino acid analysis: Gly 1.00, Met 0.32, Tyr 0.89, Phe 1.00.

EXAMPLE 42

Production of H-Tyr-(D)-Met(O)-Gly-Phe-NH-NH₂

(I) Production of H-Tyr-(D)-Met(O)-Gly-Phe-NH-NH₂

Using 300 mg of Z-Tyr-(D)-Met(O)-Gly-Phe-NH-NH₂ obtained in a similar manner to (II) of Example 27, in a similar manner to (IV) of Example 27 is obtained 140 mg of the desired product, $Rf^2=0.20$, $[\alpha]_D^{21}+33.0°$ (c=0.35, MeOH), amino acid analysis (acid hydrolyzate): Gly 1.00, Met 0.29, Tyr 0.95, Phe 1.00.

EXAMPLE 43

Production of H-Tyr-(D)-Thr-Gly-Phe-NH-NH-CO-(CH₂)₃-CH₃

(I) Production of Z-(D)-Thr-Gly-OBuᵗ

In 50 ml of THF are dissolved 5.0 g of Z-(D)-Thr-OH and 3.6 g of H-Gly-OBuᵗ. After cooling, 3.9 g of HONB and 4.5 g of DCC are added, and the mixture is stirred overnight. The solvent is distilled off, and the residue is extracted with 100 ml of AcOEt, followed by washing with water and drying over anhydrous sodium sulphate. The AcOEt is distilled off, and the residue is treated with petroleum ether. Recrystallization from AcOEt-petroleum ether yields 5.0 g of the desired compound. m.p. 56°–57° C., $[\alpha]_D^{23}+13.8°$ (c=0.5, MeOH), $Rf^1=0.69$.

Elemental analysis for $C_{18}H_{26}O_6N_2$: Calcd.: C, 59.60; H, 7.15; N, 7.65; Found: C, 58.73; H, 7.11; N, 7.87.

(II) Production of Z-Tyr-(D)-Thr-Gly-OH

In 100 ml of MeOH is dissolved 4.6 g of Z-(D)-Thr-Gly-OBuᵗ and catalytic reduction is carried out with palladium black as the catalyst. The catalyst is filtered off. After the MeOH is distilled off. the residue is dissolved in THF (50 ml). To this is added Z-Tyr-ONB (5.9 g) and the mixture is stirred overnight at room temperature. The solvent is evaporated and the residue is dissolved in AcOEt (100 ml). The AcOEt solution is washed with water, followed by drying over anhydrous sodium sulphate. The AcOEt is evaporated and the residue is treated with ether to give a powder. The powder (3.7 g) is treated with TFA (40 ml) for 40 min. at room temperature. After evaporation the residue is triturated with diethylether. The precipitate is collected. After drying, the powder is crystallized from AcOEt; yield 2.9 g. m.p. 143°–144° C., $[\alpha]_D^{23}+18.2°$ (c=0.5, MeOH), $Rf^2=0.49$.

Elemental analysis for $C_{23}H_{27}O_8N_3 \cdot \frac{1}{2}H_2O$: Calcd.: C, 57.25; H, 5.85, N, 8.87; Found: C, 57.57; H, 5.92; N, 8.55.

(III) Production of Z-Tyr-(D)-Thr-Gly-Phe-OCH$_3$

Using Z-Tyr-(D)-Thr-Gly-OH (1.5 g) and H-Phe-OCH$_3$·hydrochloride (0.73 g), 1.7 g of the desired compound is obtained in a similar manner to (I) of Example I. m.p. 102°–103° C., $[\alpha]_D^{23}+20.3°$ (c=0.33, MeOH), $Rf^1=0.44$.

Elemental analysis for $C_{33}H_{38}O_9N_4$: Calcd.: C, 62.45; H, 6.04; N, 8.83; Found: C, 62.31; H, 6.28; N, 8.59.

(IV) Production of Z-Tyr-(D)-Thr-Gly-Phe-NHNH$_2$

Using Z-Tyr-(D)-Thr-Gly-Phe-OCH$_3$ (1.5 g) and NH$_2$·NH$_2$·H$_2$O (0.5 ml), 1.4 g of the desired compound is obtained in a similar manner to (II) of Example 1. m.p. 212°–213° C., $[\alpha]_D^{23}-25.9°$ (c=0.32 DMF), $Rf^1=0.12$ Elemental analysis for $C_{32}H_{38}O_8N_6$: Calcd.: C, 60.55; H, 6.04; N, 13.24; Found: C, 60.31; H, 6.25; N, 12.98.

(V) Production of Z-Tyr-(D)-Thr-Gly-Phe-NHNH-CO-(CH$_2$)$_3$-CH$_3$

Using Z-Tyr-(D)-Thr-Gly-Phe-NHNH$_2$ (0.54 g) and n-valeric acid (0.14 ml), 0.42 g of the desired compound is obtained in a similar manner to (I) of Example 4. m.p. 172°–173° C., $[\alpha]_D^{24}-17.5°$ (c=0.39 DMF), $Rf^1=0.45$ Elemental analysis for $C_{37}H_{46}O_9N_6$: Calcd.: C, 61.82; H, 6.45; N, 11.69; Found: C, 61 66; H, 6.44; N, 11.43.

(VI) Production of H-Tyr-(D)-Thr-Gly-Phe-NHNH-CO-(CH$_2$)$_3$-CH$_3$

Using Z-Tyr-(D)-Thr-Gly-Phe-NH-NH-CO-(CH$_2$)$_3$-CH$_3$ (0.25 g) 105 mg of the desired compound is obtained in a similar manner to (II) of Example 4. $Rf^2=0.50$, $[\alpha]_D^{24}+10.8°$ (c=0.31 MeOH). Amino acid Anal. (hydrolyzed with HCl): Thr 0.97, Gly 1.00, Tyr 1.10, Phe 1.15.

EXAMPLE 44

Production of H-Tyr-(D)-Met-Gly-Phe-NHNH-CO-CH$_2$-CH$_3$ (I) Production of H-Tyr-(D)-Met-Gly-Phe-NHNH-CO-CH$_2$CH$_3$ 100 mg of H-Tyr-D-Met(O)-Gly-Phe-NHNH-CO-CH$_2$CH$_3$ is dissolved in 4% aqueous thioglycolic acid (6 ml) and kept to stand at 50° C. for 10 hr. The solution is applied to a column of Sephadex G-25, which is eluted with 30% aqueous acetic acid. The fractions (270-310 ml) are combined and lyophilized to give the desired compound; yield 80 mg. $Rf^2=0.61$ $[\alpha]_D^{21}+20.0°$ (c=0.2 MeOH).

Amino acid analysis (hydrolyzed with HCl): Gly 1.00, Met 0.77, Tyr 0.80, Phe 1.02.

EXAMPLE 45

Production of H-Tyr-(D)-Nva-Gly-Phe-NHNH-CO-CH$_3$ (I) Production of Z-Phe-NHNH-CO-CH$_3$ 115 g of Z-Phe-ONB is dissolved in THF (300 ml) and to this is added 20 g of acetylhydrazine. The mixture is stirred at room temperature for 10 hr. The formed crystals are collected by filtration, washed with water and recrystallized from acetonitrile; yield 71 g. m.p. 200°–201° C., $[\alpha]_D^{23}-17.2°$ (c=0.5, DMF), $Rf^1=0.65$.

Elemental analysis for $C_{19}H_{21}O_4N_3$: Calcd.: C, 64.21; H, 5.96; N, 11.83; Found: C, 64.05; H, 5.83; N, 11.69.

(II) Production of Z-Gly-Phe-NHNH-CO-CH$_3$

Z-Phe-NHNH-CO-CH$_3$ (42.6 g) is hydrogenated over a Pd-black in MeOH (400 ml). The mixture is filtered to remove the catalyst and the filtrate is evaporated. The residue is dissolved in DMF (100 ml), and to this is added Z-Gly-ONB (44 g).

The mixture is stirred for 10 hr. at room temperature and evaporated. The residue is treated wit diethyl ether to give a powder, which is crystallized from aqueous acetonitrile; yield 45.2 g. m.p. 154°–155° C., $[\alpha]_D^{23}-0.9°$ (c=0.5, DMF), $Rf^1=0.52$ Elemental analysis for $C_{21}H_{24}O_5N_4$: Calcd.: C, 61.15; H, 5.87; N, 13.59; Found: C, 60.89; H, 5.62; N, 13.40.

(III) Production of Z-(D)-Nva-Gly-Phe-NHNH-COCH$_3$

Z-Gly-Phe-NHNH-COCH$_3$ (5 g) is hydrogenated over a Pd-black as a catalyst in MeOH (100 ml). The catalyst is filtered and the filtrate is evaporated to give 3.5 g of H-Gly-Phe-NHNH-COCH$_3$ as crystals, H-Gly-Phe-NHNH-COCH$_3$ (0.89 g) and Z-(D)-Nva-ONB, which is prepared from Z-(D)-Nva-OH (0.80 g) and HONB (0.63 g) by the DCC method, are dissolved in DMF (10 ml). The mixture is stirred for 10 hr. at room temperature and evaporated. The residue is treated with diethylether to give a powder which is crystallized from acetonitrile; yield 1.3 g. m.p. 235°–237° C., $[\alpha]_D^{23}+3.4°$ (c=0.45, DMF), $Rf^1=0.44$.

Elemental analysis for $C_{26}H_{33}O_6N_5$: Calcd.: C, 61.04; H, 6.50; N, 13.69; Found: C, 61.33; H, 6.62; N, 13.66.

(IV) Production of Z-Tyr-(D)-Nva-Gly-Phe-NHNH-CO-CH$_3$

Z-(D)-Nva-Gly-Phe-NHNH-COCH$_3$ (0.92 g) is hydrogenated over Pd-black in MeOH (50 ml). The catalyst is filtered off and the filtrate is evaporated. The residue is dissolved in DMF (10 ml) and to this is added Z-Tyr-ONB (0.86 g). The mixture is stirred for 10 hr. at room temperature and evaporated. The residue is treated with diethylether to give a powder, which is crystallized from acetonitrille; yield 0.85 g. m.p. 210°–211° C., $[\alpha]_D^{23}-18.3°$(c=0.48, DMF), $Rf^1=0.38$.

Elemental analysis for $C_{35}H_{42}O_8N_6$: Calcd.: C, 62.30; H, 6.27; N, 12.46; Found: C, 62.15; H, 6.06; N, 12.33.

(V) Production of H-Tyr-(D)-Nva-Gly-Phe-NH-NH-COCH$_3$

Using Z-Tyr-(D)-Nva-Gly-Phe-NH-NH-COCH$_3$ (0.40 g), the desired compound (0.16 g) is obtained in a similar manner to (II) of Example 4. $Rf^2=0.36$, $[\alpha]_D^{23}+22.6°$ (c=0.30, MeOH). Amino acid analysis (hydrolized with HCl): Gly 1.00, Nva 1.10, Tyr 0.99, Phe 1.07.

EXAMPLE 46

Production of H-Tyr-(D)-Gln-Phe-NHNH-COCH$_3$ (I) Production of BOC-(D)-Gln-Phe-NHNH-COCH$_3$ Using BOC-(D)-Gln-ONP(0.96 g) and H-Gly-Phe-NHNH-COCH$_3$ (0.72 g), the desired compound (0.95 g) is obtained in a similar manner to (III) of Example 45. m.p. 198°–199° C., $[\alpha]_D^{23}$ −0.8° (C=0.50, DMF), Rf$^1$=0.19.

Elemental analysis for C$_{23}$H$_{34}$O$_7$N$_6$: Calcd.: C, 54.53; H, 6.77; N, 16.59, Found: C, 54.29; H, 6.81; N, 16.65.

(II) Production of Z-Tyr-(D)-Gln-Gly-Phe-NHNH-COCH$_3$

Using BOC-(D)-Gln-Gly-Phe-NHNH-COCH$_3$ (0.55 g) and Z-Tyr-ONB (0.52 g) the desired compound (0.60 g) is obtained in a similar manner to (V) of Example 26. m.p. 209°–210° C., $[\alpha]_D^{23}$ −21.5°(c=0.40, DMF), Rf$^1$=0.12

Elemental analysis for C$_{35}$H$_{41}$O$_9$N$_7$:

Calcd.: C, 59.73; H, 5.87; N, 13.93; Found: C, 59.72; H, 5.92; N, 13.86.

(III) Production of H-Tyr-(D)-Gln-Gly-Phe-NHNH-COCH$_3$

Using Z-Tyr-(D)-Gln-Gly-Phe-NHNH-COCH$_3$ (0.40 g), the desired compound (0.18 g) is obtained in a similar manner to (II) of Example 4. Rf$^2$=0.25, $[\alpha]_D^{23}$+14.5°(c=0.35, MeOH). Amino acid analysis (hydrolized with HCl): Glu 0.88, Gly 1.00, Tyr 0.90, Phe 0.98.

EXAMPLE 47

Production of H-Tyr-(D)-Phe-Gly-Phe-NHNH-COCH$_3$ (I) Production of BOC-(D)-Phe-Gly-Phe-NHNH-COCH$_3$ Using H-Gly-Phe-NHNH-COCH$_3$ (0.44 g) and BOC-(D)-Phe-ONB (0.68 g), the desired compound (0.68 g) is obtained in a similar manner to (III) of Example 45, m.p. 208°–209° C., $[\alpha]_D^{23}$+3.3°(c=0.45, DMF), Rf$^1$=0.51.

Elemental analysis for C$_{27}$H$_{35}$O$_6$N$_5$: Calcd.: C, 61.70; H, 6.71; N, 13.33; Found: C, 61.45; H, 6.65; N, 13.46.

(II) Production of Z-Tyr-(D)-Phe-Gly-Phe-NHNH-COCH$_3$

Using BOC-(D)-Phe-Gly-Phe-NHNH-COCH$_3$(0.51 g) and Z-Tyr-ONB(0.46 g), the desired compound is obtained in a similar manner to (V) of Example 26, m.p. 203°–204° C., $[\alpha]_D^{23}$ −13.0°(c=0.44, DMF), Rf$^1$=0.38

Elemental analysis for C$_{39}$H$_{42}$O$_8$N$_6$: Calcd.: C, 64.80; H, 5.86; N, 11.63; Found: C, 64.70; H, 5.95; N, 11.40.

(III) Production of H-Tyr-(D)-Phe-Gly-Phe-NHNH-COCH$_3$

Z-Tyr-(D)-Phe-Gly-Phe-NHNH-COCH$_3$(0.45 g) is hydrogenated in MeOH (50 ml) over Pd-black as a catalysist. The catalysist is filtered off and the filtrate is evaporated. The resulting residue is treated with diethylether to give a powder, which is crystallized from acetonitrile; yield 0.22 g, Rf$^2$=0.37. $[\alpha]_D^{23}$ −11.4°(c=0.35 MeOH).

Amino acid analysis (hydrolized with HCl): Gly 1.00, Tyr 0.98, Phe0.95.

EXAMPLE 48

Production of H-Tyr-(D)-Glu-(OCH$_3$)-Gly-Phe-NHNH-COCH$_3$ (I) Production of BOC-(D)-Glu(OCH$_3$)-Gly-Phe-NHNH-COCH$_3$ Using H-Gly-Phe-NHNH-COCH$_3$ (0.44 g) and BOC-(D)-Glu(OCH$_3$)-ONB(0.68 g), the desired compound (0.50 g) is obtained in a similar manner to (III) of Example 45. m.p. 205°–206° C., $[\alpha]_D^{23}$+2.8°(c=0.42, DMF), Rf$^1$=0.43

Elemental analysis for C$_{24}$H$_{35}$O$_8$N$_5$: Calcd.: C, 55.26; H, 6.76; N, 13.43; Found: C, 55.31; H, 6.55; N, 13.46.

(II) Production of Z-Tyr-(D)-Glu(OCH$_3$)-Gly-Phe-NHNH-COCH$_3$

Using BOC-(D)-Glu(OCH$_3$)-Gly-Phe-NHNH-COCH$_3$ (0.46 g) and Z-Tyr-ONB(0.42 g), the desired compound is obtained in a similar manner to (V) of Example 26 m.p. 200°–202° C., $[\alpha]_D^{23}$ −14.8° (c=0.44, DMF), Rf$^1$=0.31

Elemental analysis for C$_{36}$H$_{42}$O$_{10}$N$_6$: Calcd.: C, 60.16; H, 5.89; N, 11.69; Found: C, 59.53; H, 5.78; N, 11.51.

(III) Production of H-Tyr-(D)-Glu(OCH$_3$)-Gly-Phe-NHNH-COCH$_3$

Using Z-Tyr-(D)-Glu(OMe)-Gly-Phe-NHNH-COCH$_3$(0.40 g), the desired compound (0.28 g) is obtained in a similar manner to (III) of Example 47, Rf$^2$=0.27, $[\alpha]_D^{23}$+17.5° (c=0.38, MeOH), Amino acid analysis (hydrolized with HCl); Glu 0.95, Gly 1.00, Tyr 0.92, Phe 0.98.

EXAMPLE 49

Production of H-Tyr.(D)-Lys(Cl-Z)-Gly-Phe.-NHNH-COCH$_3$ (I) Production of BOC-(D)-Lys(Cl-Z)-Gly-Phe-NHNH-COCH$_3$ Using H-Gly-Phe-NHNHCOCH$_3$(0.58 g) and BOC-(D)-Lys (Cl-Z)-ONB (1.15 g), the desired compound (1.05 g) is obtained in a similar manner to (III) of Example 45, m.p. 169°–171° C., $[\alpha]_D^{23}$+4.7°(c=0.47, DMF), Rf$^1$=0.45.

Elemental analysis for C$_{32}$H$_{42}$O$_8$N$_6$Cl: Calcd.: C, 57.00; H, 6.27; N, 12.46, Cl, 5.26; Found: C, 56.88; H, 6.05; N, 12.29; Cl, 5.35.

(II) Production of BOC-Tyr-(D)-Lys(Cl-Z)-Gly-Phe-NHNH-COCH$_3$

Using BOC-(D)-Lys(Cl-Z)-Gly-Phe-NHNH-COCH$_3$ (0.70 g) and BOC-Tyr-ONB (0.50 g), the desired compound (0.71 g) is obtained in a similar manner to (V) of Example 26. m.p. 196°–198° C., $[\alpha]_D^{23}$ −2.0°(c=0.47, DMF), Rf$^1$=0.46

Elemental analysis for C$_{41}$H$_{51}$O$_{10}$N$_7$Cl: Calcd.: C, 58.80; H, 6.13; N, 11.70; Found: C, 58.69; H, 6.25; N, 11.49.

(III) Production of H-Tyr-(D)-Lys(Cl-Z)-Gly-Phe-NHNH-COCH$_3$

Using BOC-Tyr-(D)-Lys(Cl-Z)-Gly-Phe-NHNH-COCH$_3$ (0.65 g) the desired compound (0.33 g) is obtained in a similar manner to (VI) of Example 26. $Rf^2=0.42$, $[\alpha]_D^{23}+16.5°(c=0.26,$ MeOH). Amino acid analysis (hydrolized with HCl): Lys, 0.85, Gly 1.00; Tyr 0.88, Phe 1.00.

EXAMPLE 50
Production of H-Tyr-(D)-Lys-Gly-Phe-NHNH-COCH$_3$

H-Tyr-(D)-Lys(Cl-Z)-Gly-Phe-NHNH-COCH$_3$ (0.18 g) is hydrogenated over Pd-black in MeOH (50 ml). The catalyst is filtered off and the filtrate is evaporated to give to crude product, which is purified in a similar manner to (II) of Example 4; yield 0.10 g, $Rf^3=0.15$, $[\alpha]_D^{23}+26.1°$ (c=0.36, MeOH).

Amino acid analysis (hydrolized with HCl): Lys 0.98, Gly 1.00, Tyr 0.99, Phe 1.02.

EXAMPLE 51
Production of H-Tyr-(D)-Ser-Gly-Phe-NHNH-COCH$_3$ (I) Production of Z-(D)-Ser-Gly-Phe-NHNH-COCH$_3$ Using H-Gly-Phe-NHNH-COCH$_3$ (0.69 g) and Z-(D)-Ser-ONB(1.08 g), the desired compound (1.25 g) is obtained in a similar manner to (III) of Example 45. m.p. 168°–169° C., $[\alpha]_D^{23}+3.4°(c=0.5$ DMF), $Rf^1=0.25$.

Elemental analysis for $C_{24}H_{29}O_7N_5$: Calcd. C, 57.72; H, 5.85; N, 14.02: Found: C, 57.48; H, 5.99; N, 13.80.

(II) Production of Z-Tyr-(D)-Ser-Gly-Phe-NHNH-COCH$_3$

Using Z-(D)-Ser-Gly-Phe-NHNH-COCH$_3$ (0.75 and Z-Tyr-ONB (0.72 g), the desired compound is obtained in a similar manner to (IV) of Example 45. m.p. 184°–186° C., $[\alpha]_D^{23}-18.3°(c=0.30,$ DMF), $Rf^1=0.19$.

Elemental analysis for $C_{33}H_{38}O_9N_6$: Calcd.: C, 59.81; H, 5.78; N, 12.68; Found: C, 59.69; H, 5.82; N, 12.51.

(III) Production of H-Tyr-(D)-Ser-Gly-Phe-NHNH-COCH$_3$

Using Z-Tyr-(D)-Ser-Gly-Phe-NHNH-COCH$_3$ (0.40 g), the desired compound (0.21 g) is obtained in a similar manner to (II) of Example 4. $Rf^2=0.21$, $[\alpha]_D^{23}+11.4°(c=0.31,$ MeOH), Amino acid analysis (hydrolized with HCl); Ser 0.85, Gly 1.00, Tyr 0.90, Phe 0.92

EXAMPLE 52
Production of H-Tyr-(D)-His-Gly-Phe-NHNH-COCH$_2$CH$_3$ (I) Production of BOC-(D)-His(Tos)-Gly-Phe-NHNH-COCH$_2$CH$_3$ Using Z-Gly-Phe-NHNH-COCH$_2$CH$_3$ (0.85 g) and BOC-(D)-His(Tos)-ONB (1.15 g), the desired compound is obtained in a similar manner to (IV) of Example 26. m.p. 178°–179° C., $[\alpha]_D^{23}-1.7°(c=0.47,$ MeOH), $Rf^1=0.48$ Elemental analysis for $C_{32}H_{41}O_8N_7S$: Calcd.: C, 56.21; H, 6.04; N, 14.34; S, 4.69; Found: C, 56.32; H, 6.01; N, 14.15; S, 4.38.

(II) Production of BOC-(D)-His-Gly-NHNH-COCH$_2$CH$_3$

BOC-(D)-His(Tos)-Gly-Phe-NHNH-COCH$_2$CH$_3$ (0.55 g) is suspended in MeOH (15 ml) and to this is added 1 N-sodium hydroxide solution (1 ml) at 0° C. The mixture is stirred for 60 min. at room temperature and evaporated. The residue is treated with acetonitrile to give a powder, which is washed with water and dried; yield 0.29 g. m.p. 261°-263° C., $[\alpha]_D^{23}+9.5°(c=0.40,$ DMF), $Rf^2=0.38$ Elemental analysis for $C_{25}H_{35}O_6N_7 \cdot H_2O$: Calcd.: C, 54.83; H, 6.44; N, 17.90; Found: C, 54.61; H, 6.13; N, 17.80.

(III) Production of Z-Tyr-(D)-His-Gly-Phe-NHNH-COCH$_2$CH$_3$

Using BOC-(D)-His-Gly-Phe-NHNH-COCH$_2$CH$_3$ (0.25 g) and Z-Tyr-ONB (0.24 g), the desired compound (0.31 g) is obtained in a similar manner to (V) of Example 26, m.p. 181°–182° C., $[\alpha]_D^{23}-10.5°(c=0.38,$ DMF), $Rf^2=0.56$ Elemental analysis for $C_{37}H_{42}O_8N_8 \cdot H_2O$: Calcd.: C, 59.67; H, 5.68; N, 15.03; Found: C, 59.31; H, 5.92; N, 14.81.

(IV) Production of H-Tyr-(D)-His-Gly-Phe-NHNH-COCH$_2$CH$_3$

Using Z-Tyr-(D)-His-Gly-Phe-NHNH-COCH$_2$CH$_3$ (0.20 g), the desired compound (90 mg) is obtained in a similar manner to (II) of Example 4. $Rf^2=0.15$, Amino acid analysis His 0.95, Gly 1.00, Tyr 0.85, Phe 1.02

EXAMPLE 53
Production of H-Tyr-(D)-Met(O$_2$)-Gly-Phe-NHNH-CO-CH$_3$ (I) Production of BOC-(D)-Met(O$_2$)-OH.DCHA BOC-(D)-Met-OH(1.7 g) is dissolved in a mixture of MeOH (10 ml), acetic acid (10 ml) and 1 N-sulfuric acid (10 ml). To this is added 30% aqueous hydrogen peroxide (5 ml). The mixture is stirred for 24 hr. at room temperature and evaporated. The residue is extracted with AcOEt (50 ml). The AcOEt solution is washed with water and dried over anhydrous sodium sulphate. To the AcOEt solution is added DCHA (0.9 ml) and the formed crystals are collected by filtration; yield 1.8 g. m.p. 201° C., $[\alpha]_D^{23}-16.5°(c=0.18,$ DMF), $Rf^2=0.61$.

Elemental analysis for $C_{22}H_{42}O_6N_2S$: Calcd.: C, 57.11; H, 9.14; N, 6.05; S, 6.93; Found: C, 57.43; H, 9.25; N, 6.10; S, 7.08.

(II) Production of BOC-(D)-Met(O$_2$)-Gly-Phe-NHNH-COCH$_3$

Using H-Gly-Phe-NHNH-COCH$_3$ (0.69 g) and BOC-(D)-Met(O$_2$)-OH (0.66 g), the desired compound (0.67 g) is obtained in a similar manner to (III) of Example 45. m.p. 198°–199° C.(decomp.), $[\alpha]_D^{23}-2.5°(c=0.49,$ DMF), $Rf^1=0.25$.

Elemental analysis for $C_{23}H_{35}O_8N_5S$: Calcd.: C, 51.00; H, 6.51; N, 12.93; S, 5.92; Found: C, 50.92; H, 6.63; N, 12.75; S, 5.68.

(III) Production of BOC-Tyr-(D)-Met(O$_2$)-Gly-Phe-NHNH-COCH$_3$

Using BOC-(D)-Met(O$_2$)-Gly-Phe-NHNH-COCH$_3$ (0.52 g) and BOC-Tyr-ONB (0.46 g), the desired compound is obtained in a similar manner to (V) of Example 26. m.p. 176°–177° C. $[\alpha]_D^{23}-2.9°(c=0.24,$ DMF), $Rf^1=0.23$.

Elemental analysis for $C_{32}H_{44}O_{10}N_6S$: Calcd.: C, 54.52; H, 6.29; N, 11.92; S, 4.55; Found: C, 54.61; H, 6.32; N, 11.99; S, 4.62.

(IV) Production of
H-Tyr-(D)-Met(O$_2$)-Gly-Phe-NHNH-COCH$_3$

Using BOC-Tyr-(D)-Met(O$_2$)-Gly-Phe-NHNH-COCH$_3$ (0.35 g), the desired compound (0.21 g) is obtained in a similar manner to (VI) of Example 26. Rf$^2$=0.19, [α]$_D^{23}$+19.0° (c=0.33, MeOH), Amino acid analysis: Gly 1.00, Tyr 0.95, Phe 1.05.

EXAMPLE 54

Production of H-Tyr-(D)-Ala-Gly-Phe-NH-NH-CO-CH$_3$ (I) Production of
Z-Tyr-(D)-Ala-Gly-Phe-NH-NH-CO-CH$_3$ Using 0.66 g of Z-Tyr-(D)-Ala-Gly-OH and 0.59 g of Z-Phe-NH-NH-COCH$_3$, obtained in a similar manner to (II) of Example 11 is 0.82 g of the desired product, m.p. 210°-211° C., [α]$_D^{23}$−22.9°(c+0.31, DMF), Rf$^1$=0.20, Elemental analysis for C$_{33}$H$_{38}$O$_8$N$_6$·H$_2$O: Calcd.: C 59.63, H 6.07, N12.64; Found: C 59.99, H 6.28, N 12.62.

(II) Production of
H-Tyr-(D)-Ala-Gly-Phe-NHNH-CO-CH$_3$

Using 0.35 g of Z-Tyr-(D)-Ala-Gly-Phe-NHNH-CO-CH$_3$, obtained in a similar manner to (III) of Example 10 is 0.16 g of the desired product, Rf$^2$=0.40, [α]$_D^{23}$+21.6°(c=0.3, MeOH) amino acid analysis (hydrochloric acid hydrolyzate): Gly 1.00, Ala 1.02 Tyr 0.85, Phe 0.99.

EXAMPLE 55

Production of
H-Tyr-(D)-Ala-Gly-Phe-NHNH-CO-CH$_2$CH$_2$CH$_3$·hydrochloride.

80 mg of H-Tyr-(D)-Ala-Gly-Phe-NHNH-CO-CH$_2$CH$_2$CH$_3$ obtained in a similar manner to Example 10 is dissolved in 0.02 N-hydrochloric acid solution (7.5 ml), and the solution is lyophilized to give a fine powder, which is crystallized from a mixture of ethanol and acetonitrile; yield 55 mg, mp. 169°-170° C., [α]$_D^{24}$+33.1° (c=0.26 DMF).

EXAMPLE 56

Production of
H-Tyr-(D)-Met(O)-Gly-MePhe-NHNH-CO-CH$_3$ (I) Production of BOC-(D)-Met(O)-OH In 200 ml of acetonitrile is dissolved 37 g of BOC-(D)-Met-OH, followed by adding 19 ml of a 30% aqueous solution of hydrogen peroxide, and the mixture is stirred for 8 hours at room temperature. Palladium black is added to the reaction mixture, and then the mixture is stirred for one hour. Palladium black is filtered off, and then acetonitrile is distilled off. The residue is extracted with 300 ml of n-butanol. The n-butanol layer is washed with aqueous solution of NaCl, and then n-butanol is distilled off. The residue is recrystallized from diethyl ether and, then, AcOEt-diethyl ether to give 32 g of crystals, m.p. 125°-126° C., [α]$_D^{23}$+7.2° (C=0.5, DMF), Rf$^1$=0.27.

Elemental analysis for C$_{10}$H$_{19}$O$_5$N$_1$S: Calcd.: C, 45.26; H, 7.21; N, 5.27; S, 12.08; Found: C, 45.31; H, 7.27, N, 5.01; S, 11.83.

(II) Production of
BOC-(D)-Met(O)-Gly-MePhe-NHNH-CO-CH$_3$

In 20 ml of THF are dissolved 3.1 g of Z-MePhe-OH and 1.9 g of HONB, and followed by adding 2.3 g of DCC under ice-cooling. The mixture is stirred for 4 hours at 0° C. The insolubles are removed by filtration, and to the filtrate is added 0.9 g of NH$_2$-NH-COCH$_3$, followed by stirring for 3 hours at room temperature. The THF is distilled off and the residue is extracted with 100 ml of AcOEt. The extract is washed with water and dried over anhydrous sodium sulfate.

The AcOEt is distilled off and the residue is dissolved in 100 ml of MeOH to carry out catalytic reduction with palladium black as the catalst.

Following the removal of the catalyst by filtration, MeOH is distilled off, whereby crystals are precipitated. To the crystals is added 10 ml of petroleum ether, and the crystals are recovered by filtration from the mixture. In 30 ml of acetonitrile are dissolved 1.3 g of the crystals and 2.0 g of BOC-Gly-ONB, and the mixture is stirred overnight at room temperature. The solvent is distilled off, and the residue is extracted with 100 ml of AcOEt. The extract is washed with water and then dried over anhydrous sodium sulfate, followed by removing AcOEt by distillation to give 2.3 g of oily product. In 20 ml of TFA is dissolved the oily product, and the mixture is allowed to stand for 20 minutes at room temperature. The TFA is distilled off, and to the residue is added diethyl ether.

The mixture is washed by means of decantation. To thus obtained product is added 20 ml of DMF. To the mixture are added 0.8 ml of TEA and 1.3 g of BOC-(D)-Met(O)-ONB (prepared by means of DCC method with 1.3 g of BOC-(D)-Met(O)-OH and 1.0 g of HONB) under ice-cooling, followed by stirring overnight at room temperature. The DMF is distilled off, and the residue is extracted with 100 ml of n-butanol. The extract is washed with water, and n-butanol is distilled off. The residue is treated with diethyl ether and reprecipitated with methanol-diethyl ether to give 1.5 g of precipitate, m.p. 119°-121° C., [α]$_D^{24}$−29.0°(c=0.38, DMF), Rf$^1$=0.19.

Elemental analysis for C$_{24}$H$_{37}$O$_7$N$_5$S·H$_2$O: Calcd.: C, 51.69; H, 7.05; N, 12.56; S, 5.05; Found: C, 51.64; H, 7.18; N, 12.11; S, 5.76.

(III) Production of
BOC-Tyr-(D)-Met(O)-Gly-MePhe-NHNH-CO-CH$_3$

Using 0.54 g of BOC-(D)-Met(O)-Gly-MePhe-NHNH-CO-CH$_3$ and 0.46 g of BOC-Tyr-ONB in a similar manner to (III) of Example 36 is obtained (0.46 g) of the desired product, m.p. 141°-142° C., [α]$_D^{22}$−25.4° (c=0.48, DMF), Rf$^1$=0.22.

Elemental analysis for C$_{33}$H$_{46}$O$_9$N$_6$S.·2H$_2$O: Calcd.: C, 53.64; H, 6.81; N, 11.37; S, 4.34; Found: C, 53.15; H, 6.65; N, 10.77; S, 4.23.

(IV) Production of
H-Tyr-(D)-Met(O)-Gly-MePhe-NHNH-CO-CH$_3$

Using 0.35 g of BOC-Tyr-(D)-Met(O)-Gly-MePhe-NHNH-CO-CH$_3$, in a similar manner to (IV) of Example 36 is obtained 0.19 g of the desired product, [α]$_D^{22}$0° (c=0.25, MeOH), Rf$^2$=0.16, amino acid analysis: Gly 1.00, Met 1.00, Tyr 1.20.

Example 57

Production of H-MeTyr-(D)-Met(O)-Gly-Phe-NHNH-CO-CH₃

(I) Production of Z-Phe-NHNH-CO-CH₃

In 50 ml of THF is dissolved 2.0 g of Z-Phe-NHNH₂, followed by adding 1.4 ml of anhydrous acetic acid and 0.9 ml of TEA under ice-cooling, and the mixture is stirred for 2 hours at room temperature. The precipitated crystals are collected by filtration, washed well with diethyl ether and recrystallized from ethyl acetate to give 1.9 g of crystals, m.p. 205°–206° C., $[\alpha]_D^{23} -16.4°$ (c=0.50, DMF), $Rf^1 = 0.60$.

Elemental analysis for $C_{20}H_{23}O_5N_3$: Calcd.: C, 62.32; H, 6.02; N, 10.90; Found: C, 62.38; H, 6.09; N, 10.49.

(II) Production of Z-Gly-Phe-NHNH-CO-CH₃

Using 2.1 g of Z-Phe-NHNH-CO-CH₃ and 2.2 g of Z-Gly-ONB, in a similar manner to (III) of Example 26 is obtained the desired product, m.p. 154°–155° C., $[\alpha]_D^{23} -0.9°$ (c=0.50, DMF), $Rf^1 = 0.52$.

Elemental analysis for $C_{21}H_{24}O_5N_4$: Calcd.: C, 61.15; H, 5.87, N, 13.59; Found: C, 60.98; H, 5.68, N, 13.27.

(III) Production of BOC-(D)-Met(O)-Gly-Phe-NHNH-CO-CH₃

Using 0.60 g of BOC-(D)-Met-OH and 1.0 g of Z-Gly-Phe-NHNH-CO-CH₃, in a similar manner to (IV) of Example 26 is obtained 1.0 g of the desired product, m.p. 122°–123° C., $[\alpha]_D^{21}$ 0° (c=0.5, DMF), $Rf^1 = 0.38$.

Elemental analysis for $C_{23}H_{35}O_7N_5S$:
Calcd.: C, 52.56; H, 6.72; N, 13.32, S, 6.09;
Found: C, 52.35; H, 6.62; N, 13.12, S, 5.93.

(IV) Production of Z-MeTyr(Buᵗ)-(D)-Met(O)-Gly-Phe-NHNH-CO-CH₃

Using 0.55 g of BOC-(D)-Met(O)-Gly-Phe-NHNH-CO-CH₃ and 0.39 g of Z-MeTyr(Buᵗ)-OH, in a similar manner to (I) of Example 37 is obtained 0.61 g of the desired product, m.p. 140°–142° C., $[\alpha]_D^{21} -29.0°$ (c=0.5, DMF), $Rf^1 = 0.43$.

Elemental anlysis for $C_{40}H_{52}O_9N_6S$: Calcd.: C, 60.59; H, 6.61; N, 10.59; S, 4.04; Found: C, 60.28; H, 6.55; N, 10.28; S, 3.88.

(V) Production of H-MeTyr-(D)-Met(O)-Gly-Phe-NHNH-CO-CH₃

Using 300 mg of Z-MeTyr(Buᵗ)-(D)-Met(O)-Gly-Phe-NHNH-CO-CH₃, in a similar manner to (IV) of Example 27 is obtained 110 mg of the desired product, $[\alpha]_D^{21} +18.5°$ (c=0.25, MeOH), $Rf^2 = 0.29$.

Amino acid analysis: Gly 1.00, Met 0.35, Phe 0.99

Example 58

Production of H-MeTyr-(D)-Met(O)-Gly-MePhe-NHNH-CO-CH₃

(I) Production of Z-MeTyr(Buᵗ)-(D)-Met(O)-Gly-MePhe-NHNH-CO-CH₃

Using 0.50 g of BOC-(D)-Met(O)-Gly-MePhe-NHNH-CO-CH₃ and 0.39 g of Z-MeTyr(Buᵗ)-OH, in a similar manner to (I) of Example 38 is obtained 0.40 g of the desired product, m.p. 120°–122° C., $Rf^1 = 0.46$.

Elemental analysis for $C_{41}H_{54}O_9N_6S$: Calcd.: C, 61.02; H, 6.74; N, 10.42; S, 3.97; Found: C, 60.79; H, 6.82; N, 9.92; S, 3.81.

(II) Production of H-MeTyr-(D)-Met(O)-Gly-MePhe-NHNH-CO-CH₃

Using 0.20 g of Z-MeTyr(Buᵗ)-(D)-Met(O)-Gly-MePhe-NHNH-CO-CH₃, in a similar manner to (IV) of Example 27 is obtained 0.90 g of the desired product, $Rf^2 = 0.34$. Amino acid analysis: Gly 1.00, Met 0.38.

What we claim is:

1. A tetrapeptidehydrazide derivative, inclusive of a pharmacologically acceptable acid addition salt thereof, which has the general formula:

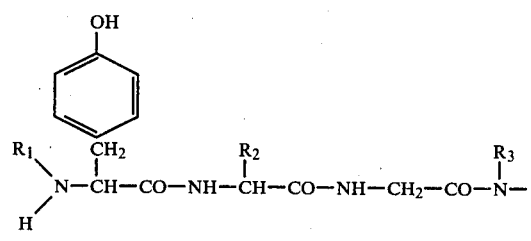
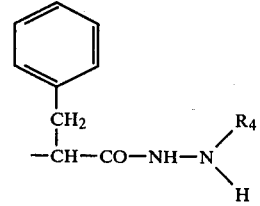

[wherein $R_1$ is hydrogen or lower alkyl; $R_2$ is hydrogen or the side chain of a D-α-amino acid; $R_3$ is hydrogen or lower alkyl; $R_4$ is hydrogen, or a saturated or unsaturated and straight or branched lower aliphatic acyl group which may optionally be substituted by hydroxyl, amino, lower alkoxy, halogen, oxo, lower thioalkyl or lower thioalkyloxide].

2. The tetrapeptidehydrazide as claimed in claim 1, wherein $R_1$ is lower alkyl having 1 to 6 carbon atoms.

3. The tetrapeptidehydrazide as claimed in claim 1, wherein $R_1$ is hydrogen.

4. The tetrapeptidehydrazide as claimed in claim 2, wherein $R_1$ is methyl.

5. The tetrapeptidehydrazide as claimed in claim 1, wherein $R_2$ is the side chain of D-leucine.

6. The tetrapeptidehydrazide as claimed in claim 1, wherein $R_2$ is the side chain of D-ananine.

7. The tetrapeptidehydrazide as claimed in claim 1, wherein $R_2$ is the side chain of D-methionine.

8. The tetrapeptidehydrazide as claimed in claim 1, wherein $R_2$ is the side chain of D-methionine sulfoxide.

9. The tetrapeptidehydrazide as claimed in claim 1, wherein $R_2$ is the side chain of D-threonine.

10. The tetrapeptidehydrazide as claimed in claim 1, wherein $R_2$ is the side chain of D-norvaline.

11. The tetrapeptidehydrazide as claimed in claim 1, wherein $R_2$ is the side chain of D-glutamine.

12. The tetrapeptidehydrazide as claimed in claim 1, wherein $R_2$ is the side chain of D-phenylalanine.

13. The tetrapeptidehydrazide as claimed in claim 1, wherein $R_2$ is the side chain of D-glutamic acid.

14. The tetrapeptidehydrazide as claimed in claim 1, wherein $R_2$ is the side chain of D-lysine.

15. The tetrapeptidehydrazide as claimed in claim 1, wherein $R_2$ is the side chain of D-serine.

16. The tetrapeptidehydrazide as claimed in claim 1, wherein $R_2$ is the side chain of D-histidine.

17. The tetrapeptidehydrazide as claimed in claim 1, wherein $R_2$ is the side chain of D-methionine sulfone.

18. The tetrapeptidehydrazide as claimed in claim 1, wherein $R_2$ is the side chain of D-methionine sulfoxide and $R_4$ is hydrogen.

19. The tetrapeptidehydrazide as claimed in claim 1, wherein $R_3$ is lower alkyl having 1 or 2 carbon atoms.

20. The tetrapeptidehydrazide as claimed in claim 19, wherein $R_3$ is methyl.

21. The tetrapeptidehydrazide as claimed in claim 1, wherein $R_4$ is hydrogen.

22. The tetrapeptidehydrazide as claimed in claim 1, wherein the parent lower aliphatic acyl $R_4$ has 1 to 8 carbon atoms.

23. The tetrapeptidehydrazide as claimed in claim 22, wherein the parent lower aliphatic acyl $R_4$ has 2 to 6 carbon atoms.

24. The tetrapeptidehydrazide as claimed in claim 22, wherein the parent lower aliphatic acyl $R_4$ has 3 to 5 carbon atoms.

25. The tetrapeptidehydrazide as claimed in claim 22, wherein the parent lower aliphatic acyl $R_4$ is acetyl.

26. The tetrapeptidehydrazide as claimed in claim 22, wherein the parent lower aliphatic acyl $R_4$ is propionyl.

27. The tetrapeptidehydrazide as claimed in claim 22, wherein the parent lower aliphatic acyl $R_4$ is butyryl.

28. The tetrapeptidehydrazide as claimed in claim 22, wherein the parent lower aliphatic acyl $R_4$ is isobutyryl.

29. The tetrapeptidehydrazide as claimed in claim 22, wherein the parent lower aliphatic acyl $R_4$ is valeryl.

30. The tetrapeptidehydrazide as claimed in claim 22, wherein the parent lower aliphatic acyl $R_4$ is isovaleryl.

31. The tetrapeptidehydrazide as claimed in claim 1, wherein the substituted lower aliphatic acyl group $R_4$ is 2-hydroxypropionyl.

32. The tetrapeptidehydrazide as claimed in claim 1, wherein the substituted lower aliphatic acyl group $R_4$ is 3-hydroxypropionyl.

33. The tetrapeptidehydrazide as claimed in claim 1, wherein the substituted lower aliphatic acyl group $R_4$ is methylthioacetyl.

34. The tetrapeptidehydrazide as claimed in claim 1, wherein $R_1$ is hydrogen, $R_2$ is the side chain of D-leucine, $R_3$ is hydrogen and $R_4$ is hydrogen.

35. The tetrapeptidehydrazide as claimed in claim 1, wherein $R_1$ is hydrogen, $R_2$ is the side chain of D-alanine, $R_3$ is hydrogen and $R_4$ is hydrogen.

36. The tetrapeptidehydrazide as claimed in claim 1, wherein $R_1$ is hydrogen, $R_2$ is the side chain of D-leucine, $R_3$ is hydrogen and $R_4$ is acetyl.

37. The tetrapeptidehydrazide as claimed in claim 1, wherein $R_1$ is hydrogen, $R_2$ is the side chain of D-alanine, $R_3$ is hydrogen and $R_4$ is valeryl.

38. The tetrapeptidehydrazide as claimed in claim 1, wherein $R_1$ is hydrogen, $R_2$ is the side chain of D-alanine, $R_3$ is hydrogen and $R_4$ is isovaleryl.

39. The tetrapeptidehydrazide as claimed in claim 1, wherein $R_1$ is hydrogen, $R_2$ is the side chain of D-alanine, $R_3$ is hydrogen and $R_4$ is 3-chloropropionyl.

40. The tetrapeptidehydrazide as claimed in claim 1, wherein $R_1$ is hydrogen, $R_2$ is the side chain of D-alanine, $R_3$ is hydrogen and $R_4$ is 3-hydroxypropionyl.

41. The tetrapeptidehydrazide as claimed in claim 1, wherein $R_1$ is hydrogen, $R_2$ is the side chain of D-alanine, $R_3$ is hydrogen and $R_4$ is propionyl.

42. The tetrapeptidehydrazide as claimed in claim 1, wherein $R_1$ is hydrogen, $R_2$ is the side chain of D-alanine, $R_3$ is hydrogen and $R_4$ is 3-aminopropionyl.

43. The tetrapeptidehydrazide as claimed in claim 1, wherein $R_1$ is hydrogen, $R_2$ is the side chain of D-alanine, $R_3$ is hydrogen and $R_4$ is n-butyryl.

44. The tetrapeptidehydrazide as claimed in claim 1, wherein $R_1$ is hydrogen, $R_2$ is the side chain of D-alanine, $R_3$ is hydrogen and $R_4$ is ethoxyformyl.

45. The tetrapeptidehydrazide as claimed in claim 1, wherein $R_1$ is hydrogen, $R_2$ is the side chain of D-alanine, $R_3$ is methyl and $R_4$ is hydrogen.

46. The tetrapeptidehydrazide as claimed in claim 1, wherein $R_1$ is hydrogen, $R_2$ is the side chain of D-alanine, $R_3$ is hydrogen and $R_4$ is 4-chlorobutyryl.

47. The tetrapeptidehydrazide as claimed in claim 1, wherein $R_1$ is hydrogen, $R_2$ is the side chain of D-alanine, $R_3$ is methyl and $R_4$ is propionyl.

48. The tetrapeptidehydrazide as claimed in claim 1, wherein $R_1$ is hydrogen, $R_2$ is the side chain of D-alanine, $R_3$ is methyl and $R_4$ is n-butyryl.

49. The tetrapeptidehydrazide as claimed in claim 1, wherein $R_1$ is hydrogen, $R_2$ is the side chain of D-alanine, $R_3$ is methyl and $R_4$ is 4-oxovaleryl.

50. The tetrapeptidehydrazide as claimed in claim 1, wherein $R_1$ is methyl, $R_2$ is the side chain of D-alanine, $R_3$ is hydrogen and $R_4$ is propionyl.

51. The tetrapeptidehydrazide as claimed in claim 1, wherein $R_1$ is methyl, $R_2$ is the side chain of D-alanine, $R_3$ is methyl and $R_4$ is propionyl.

52. The tetrapeptidehydrazide as claimed in claim 1, wherein $R_1$ is hydrogen, $R_2$ is the side chain of D-alanine, $R_3$ is methyl and $R_4$ is acetyl.

53. The tetrapeptidehydrazide as claimed in claim 1, wherein $R_1$ is hydrogen, $R_2$ is the side chain of D-alanine, $R_3$ is methyl and $R_4$ is 3-ethoxypropionyl.

54. The tetrapeptidehydrazide as claimed in claim 1, wherein $R_1$ is hydrogen, $R_2$ is the side chain of D-alanine, $R_3$ is methyl and $R_4$ is isovaleryl.

55. The tetrapeptidehydrazide as claimed in claim 1, wherein $R_1$ is hydrogen, $R_2$ is the side chain of D-alanine, $R_3$ is methyl and $R_4$ is 3-chloropropionyl.

56. The tetrapeptidehydrazide as claimed in claim 1, wherein $R_1$ is hydrogen, $R_2$ is the side chain of D-alanine, $R_3$ is methyl and $R_4$ is 2-hydroxypropionyl.

57. The tetrapeptidehydrazide as claimed in claim 1, wherein $R_1$ is hydrogen, $R_2$ is the side chain of D-alanine, $R_3$ is methyl and $R_4$ is ethoxyformyl.

58. The tetrapeptidehydrazide as claimed in claim 1, wherein $R_1$ is hydrogen, $R_2$ is the side chain of D-alanine, $R_3$ is methyl and $R_4$ is valeryl.

59. The tetrapeptidehydrazide as claimed in claim 1, wherein $R_1$ is hydrogen, $R_2$ is the side chain of D-methionine sulfoxide, $R_3$ is hydrogen and $R_4$ is propionyl.

60. The tetrapeptidehydrazide as claimed in claim 1, wherein $R_1$ is hydrogen, $R_2$ is the side chain of D-methionine sulfoxide, $R_3$ is hydrogen and $R_4$ is n-butyryl.

61. The tetrapeptidehydrazide as claimed in claim 1, wherein $R_1$ is hydrogen, $R_2$ is the side chain of D-methionine sulfoxide, $R_3$ is hydrogen and $R_4$ is isobutyryl.

62. The tetrapeptidehydrazide as claimed in claim 1, wherein $R_1$ is hydrogen, $R_2$ is the side chain of D-methionine sulfoxide, $R_3$ is hydrogen and $R_4$ is acetyl.

63. The tetrapeptidehydrazide as claimed in claim 1, wherein $R_1$ is hydrogen, $R_2$ is the side chain of D-methionine sulfoxide, $R_3$ is hydrogen and $R_4$ is valeryl.

64. The tetrapeptidehydrazide as claimed in claim 1, wherein $R_1$ is hydrogen, $R_2$ is the side chain of D-methionine sulfoxide, $R_3$ is hydrogen and $R_4$ is hexanoyl.

65. The tetrapeptidehydrazide as claimed in claim 1, wherein $R_1$ is hydrogen, $R_2$ is the side chain of D-methionine sulfoxide, $R_3$ is hydrogen and $R_4$ is 3-ethoxypropionyl.

66. The tetrapeptidehydrazide as claimed in claim 1, wherein $R_1$ is hydrogen, $R_2$ is the side chain of D-methionine sulfoxide, $R_3$ is hydrogen and $R_4$ is ethoxyformyl.

67. The tetrapeptidehydrazide as claimed in claim 1, wherein $R_1$ is hydrogen, $R_2$ is the side chain of D-methionine sulfoxide, $R_3$ is hydrogen and $R_4$ is methylthioacetyl.

68. The tetrapeptidehydrazide as claimed in claim 1, wherein $R_1$ is hydrogen, $R_2$ is the side chain of D-methionine sulfoxide, $R_3$ is hydrogen and $R_4$ is methylthiooxideacetyl.

69. The tetrapeptidehydrazide as claimed in claim 1, wherein $R_1$ is hydrogen, $R_2$ is the side chain of D-methionine sulfoxide, $R_3$ is methyl and $R_4$ is propionyl.

70. The tetrapeptidehydrazide as claimed in claim 1, wherein $R_1$ is methyl, $R_2$ is the side chain of D-methionine sulfoxide, $R_3$ is hydrogen and $R_4$ is propionyl.

71. The tetrapeptidehydrazide as claimed in claim 1, wherein $R_1$ is methyl, $R_2$ is the side chain of D-methionine sulfoxide, $R_3$ is methyl and $R_4$ is propionyl.

72. The tetrapeptidehydrazide as claimed in claim 1, wherein $R_1$ is hydrogen, $R_2$ is the side chain of D-methionine sulfoxide, $R_3$ is hydrogen and $R_4$ is 3-chloropropionyl.

73. The tetrapeptidehydrazide as claimed in claim 1, wherein $R_1$ is hydrogen, $R_2$ is the side chain of D-methionine sulfoxide, $R_3$ is hydrogen and $R_4$ is 4-oxovaleryl.

74. The tetrapeptidehydrazide as claimed in claim 1, wherein $R_1$ is hydrogen, $R_2$ is the side chain of D-methionine sulfoxide, $R_3$ is hydrogen and $R_4$ is 3-hydroxypropionyl.

75. The tetrapeptidehydrazide as claimed in claim 1, wherein $R_1$ is hydrogen, $R_2$ is the side chain of D-methionine sulfoxide, $R_3$ is hydrogen and $R_4$ is hydrogen.

76. The tetrapeptidehydrazide as claimed in claim 1, wherein $R_1$ is hydrogen, $R_2$ is the side chain of D-threonine, $R_3$ is hydrogen and $R_4$ is valeryl.

77. The tetrapeptidehydrazide as claimed in claim 1, wherein $R_1$ is hydrogen, $R_2$ is the side chain of D-methionine, $R_3$ is hydrogen and $R_4$ is propionyl.

78. The tetrapeptidehydrazide as claimed in claim 1, wherein $R_1$ is hydrogen, $R_2$ is the side chain of D-norvaline, $R_3$ is hydrogen and $R_4$ is propionyl.

79. The tetrapeptidehydrazide as claimed in claim 1, wherein $R_1$ is hydrogen, $R_2$ is the side chain of D-glutamine, $R_3$ is hydrogen and $R_4$ is propionyl.

80. The tetrapeptidehydrazide as claimed in claim 1, wherein $R_1$ is hydrogen, $R_2$ is the side chain of D-phenylalanine, $R_3$ is hydrogen and $R_4$ is propionyl.

81. The tetrapeptidehydrazide as claimed in claim 1, wherein $R_1$ is hydrogen, $R_2$ is the side chain of D-glutamic acid-$\gamma$-methylester, $R_3$ is hydrogen and $R_4$ is propionyl.

82. The tetrapeptidehydrazide as claimed in claim 1, wherein $R_1$ is hydrogen, $R_2$ is the side chain of $\epsilon$-p-chlorobenzyloxycarbonyl-D-lysine, $R_3$ is hydrogen and $R_4$ is propionyl.

83. The tetrapeptidehydrazide as claimed in claim 1, wherein $R_1$ is hydrogen, $R_2$ is the side chain of D-lysine, $R_3$ is hydrogen and $R_4$ is propionyl.

84. The tetrapeptidehydrazide as claimed in claim 1, wherein $R_1$ is hydrogen, $R_2$ is the side chain of D-serine, $R_3$ is hydrogen and $R_4$ is propionyl.

85. The tetrapeptidehydrazide as claimed in claim 1, wherein $R_1$ is hydrogen, $R_2$ is the side chain of D-histidine, $R_3$ is hydrogen and $R_4$ is propionyl.

86. The tetrapeptidehydrazide as claimed in claim 1, wherein $R_1$ is hydrogen, $R_2$ is the side chain of D-methionine sulfone, $R_3$ is hydrogen and $R_4$ is propionyl.

87. The tetrapeptidehydrazide as claimed in claim 1, wherein $R_1$ is hydrogen, $R_2$ is the side chain of D-alanine, $R_3$ is hydrogen and $R_4$ is propionyl.

88. The tetrapeptidehydrazide as claimed in claim 1, wherein $R_1$ is hydrogen, $R_2$ is the side chain of D-methionine sulfoxide, $R_3$ is methyl and $R_4$ is acetyl.

89. The tetrapeptidehydrazide as claimed in claim 1, wherein $R_1$ is methyl, $R_2$ is the side chain of D-methionine sulfoxide, $R_3$ is hydrogen and $R_4$ is acetyl.

90. The tetrapeptidehydrazide as claimed in claim 1, wherein $R_1$ is methyl, $R_2$ is the side chain of D-methionine sulfoxide, $R_3$ is methyl and $R_4$ is acetyl.

* * * * *